(12) United States Patent
Shi et al.

(10) Patent No.: US 11,619,635 B2
(45) Date of Patent: Apr. 4, 2023

(54) PROCESS FOR ULTRA-SENSITIVE QUANTIFICATION OF TARGET ANALYTES IN COMPLEX BIOLOGICAL SYSTEMS

(71) Applicant: BATTELLE MEMORIAL INSTITUTE, Richland, WA (US)

(72) Inventors: Tujin Shi, Richland, WA (US); Weijun Qian, Richland, WA (US); Thomas L. Fillmore, Kennewick, WA (US); Xuefei Sun, Richland, WA (US); Richard D. Smith, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 89 days.

(21) Appl. No.: 14/949,385

(22) Filed: Nov. 23, 2015

(65) Prior Publication Data

US 2016/0238614 A1    Aug. 18, 2016

Related U.S. Application Data

(63) Continuation of application No. 13/736,279, filed on Jan. 8, 2013, now abandoned.

(51) Int. Cl.
*G01N 33/68* (2006.01)
*G01N 30/86* (2006.01)
(Continued)

(52) U.S. Cl.
CPC ......... *G01N 33/6848* (2013.01); *G01N 33/50* (2013.01); *G01N 33/6842* (2013.01);
(Continued)

(58) Field of Classification Search
CPC ........... G01N 33/6848; G01N 33/6842; G01N 33/50; G01N 2560/00; G01N 2458/15;
(Continued)

(56) References Cited

U.S. PATENT DOCUMENTS 3,651,042 A * 3/1972 Cooper et al. ....... C07H 15/236
536/13.6
2006/0006326 A1 * 1/2006 Belov ................. G01N 30/7233
250/282

(Continued)

FOREIGN PATENT DOCUMENTS

WO    WO 2012/021969    2/2012
WO    PCT/US2013/066773    1/2014
WO    PCT/US2013/066773    7/2015

OTHER PUBLICATIONS

Shi et al. (PNAS, Sep. 18, 2012 vol. 109, No. 38, pp. 15395-15400) (Year: 2012).*

(Continued)

*Primary Examiner* — Jill A Warden
(74) *Attorney, Agent, or Firm* — Wells St. John P.S.

(57) ABSTRACT

Antibody-free processes are disclosed that provide accurate quantification of a wide variety of low-abundance target analytes in complex samples. The processes can employ high-pressure, high-resolution chromatographic separations for analyte enrichment. Intelligent selection of target fractions may be performed via on-line Selected Reaction Monitoring (SRM) or off-line rapid screening of internal standards. Quantification may be performed on individual or multiplexed fractions. Applications include analyses of, e.g., very low abundance proteins or candidate biomarkers in plasma, cell, or tissue samples without the need for affinity-specific reagents.

10 Claims, 6 Drawing Sheets

Specification includes a Sequence Listing.

(51) Int. Cl.
*G01N 33/50* (2006.01)
*G01N 30/72* (2006.01)
*G01N 30/88* (2006.01)

(52) U.S. Cl.
CPC ......... *G01N 30/72* (2013.01); *G01N 30/8631* (2013.01); *G01N 2030/8831* (2013.01); *G01N 2458/15* (2013.01); *G01N 2560/00* (2013.01)

(58) Field of Classification Search
CPC ....... G01N 2030/8831; G01N 30/8631; G01N 30/72
See application file for complete search history.

(56) References Cited

U.S. PATENT DOCUMENTS

| | | | | |
|---|---|---|---|---|
| 2008/0277578 | A1* | 11/2008 | Ferrari | B01D 15/00 250/288 |
| 2011/0240842 | A1 | 10/2011 | Grant et al. | |
| 2012/0187284 | A1* | 7/2012 | Geyer | H01J 49/0009 250/252.1 |
| 2012/0288873 | A1* | 11/2012 | Diamandis | C12Q 1/37 435/7.4 |
| 2012/0309040 | A1* | 12/2012 | Madian | G01N 33/6842 435/23 |
| 2013/0080073 | A1* | 3/2013 | de Corral | G01N 30/86 702/23 |

OTHER PUBLICATIONS

Gallien et al.(Journal of Mass Spectrometry, 2011, pp. 298-312). (Year: 2011).*
Dionex Technical Note 85 (2009, pp. 1-12) (Year: 2009).*
Lange et al.(Molecular Systems Biology, 4(222), 2008, pp. 1-14 (Year: 2008).*
Fisher et al. (Proteomics Clin Appl. Dec. 2011; 5(0): 603-612.) (Year: 2011).*
Fortin, et al. "Clinical Quantitation of Prostate-specific Antigen Biomarker in the Low Nanogram/Milliliter Range by Conventional Bore Liquid Chromatography-Tandem Mass Spectrometry (Multiple Reaction Monitoring) Coupling and Correlation with ELISA Tests," Molecular & Cellular Proteomics, 8, 2009, pp. 1006-1015.*
Krastins, et al. "Using Discovery Information to Build Intelligent Targeted Selected Reaction Monitoring (SMR) Assays for Phosphopeptides," Sep. 23, 2009, article retrieved from the Internet, URL: <http://www.thermofisher.com.au/Uploads/file/Scientific/Applications/Life-Science-Research-Technologies, 1 page.*
Addona et al., "A Pipeline That Integrates the Discovery and Verification of Plasma Protein Biomarkers Reveals Candidate Markers for Cardiovascular Disease", Nature Biotechnology, 29, 7, 2011, pp. 635-643.
Addona et al., "Multi-site Assessment of the Precision and Reproducibility of Multiple Reaction Monitoring-Based Measurements of Proteins in Plasma", Nature Biotechnology, 27, 7, 2009, pp. 633-641.
Anderson et al., "Mass Spectrometric Quantitation of Peptides and Proteins Using Stable Isotope Standards and Capture by Anti-Peptide Antibodies (SISCAPA)", Journal of Proteome Research, 3, 2004, pp. 235-244.
Anderson et al., "Quantitative Mass Spectrometric Multiple Reaction Monitoring Assays for Major Plasma Proteins*", Molecular & Cellular Proteomics, 5, 2006, pp. 573-588.
Biemann, "Contributions of Mass Spectrometry to Peptide and Protein Structure", Biomedical and Environmental Mass Spectrometry, 1988, vol. 16, pp. 99-111.
Bisson et al., "Selected Reaction Monitoring Mass Spectrometry Reveals ths Dynamics of Signaling Through the GRB2 Adaptor", Nature Biotechnology, 29, 7, 2011, pp. 653-658.

Cho et al., "Verification of a Biomarker Discovery Approach for Detection of Down Syndrome in Amniotic Fluid Via Multiplex Selected reaction Monitoring (SRM) Assay", Journal of Proteomics, 2011, 74, pp. 2052-2059.
Dionex Technical Note, 2009, 12 pages.
Gallien et al., "Selected reaction monitoring applied to proteomics", Journal of Mass Spectrom., 2011, pp. 298-312.
Gerber et al., "Absolute Quantification of Proteins and Phosphoproteins from Cell Lysates by Tandem MS", PNAS, 100, 12, Jun. 10, 2003, pp. 6940-6945.
Gilar et al., "Two-Dimensional Separation of Peptides Using RP-RP-HPLC System with Different pH in First and Second Separation Dimensions", J. Sep. Sci., 28, 2005, pp. 1694-1703.
Held et al., "Targeted Quantitation of Site-Specific Cysteine Oxidation in Endogenous Proteins Using a Differential Alkylation and Multiple Reaction Monitoring Mass Spectrometry Approach", Molecular & Cellular Proteomics, 9, 2010, pp. 1400-1410.
Hoofnagle et al., "Quantification of Thyroglobulin, a Low-Abundance Serum Protein, by Immunoaffinity Peptide Enrichment and Tandem Mass Spectrometry", Proteomics and Protein Markers, 54, 11, 2008, pp. 1796-1804.
Hossain et al., "Enhanced Sensitivity for Selected Reaction Monitoring Mass Spectrometry-based Targeted Proteomics Using a Dual Stage Electrodynamic Ion Funnel Interface*", Molecular & Cellular Proteomics, 10, 2011, pp. M000062-MCP201.
Jovanovic et al., "A Quantitative Targeted Proteomics Approach to Validate Predicted MicroRNA Targets in C. elegans", Nature Methods, 7, 10, 2010, pp. 837-842.
Keshishian et al., "Quantification of Cardiovascular Biomarkers in Patient Plasma by Targeted Mass Spectrometry and Stable Isotope Dilution*", Molecular & Cellular Proteomics, 8, 2009, pp. 2339-2349.
Keshishian et al., "Quantitative, Multiplexed Assays for Low Abundance Proteins in Plasma by Targeted Mass Spectrometry and Stable Isotope Dilution*", Molecular & Cellular Proteomics, 6, 2007, pp. 2212-2229.
Kiyonami et al., "Increased Selectivity, Analytical Precision, and Throughput in Targeted Proteomics, Molecular and Cellular Proteomics", Jul. 27, 2010, pp. 1-11.
Kuhn et al., "Developing Multiplexed Assays for Troponin 1 and Interleukin-33 in Plasma by Peptide Immunoaffinity Enrichment and Targeted Mass Spectrometry", Clinical Chemistry, 55, 6, 2009, pp. 1108-1117.
Kuzyk et al., "Multiple Reaction Monitoring-Based, Multiplexed, Absolute Quantitation of 45 Proteins in Human Plasma*", Molecular & Cellular Proteomics, 8, 2009, pp. 1860-1877.
Lange et al., "Selected Reaction Monitoring for Quantitative Proteomics: A Tutorial, Molecular Systems Biology", 4, 2008, pp. 1-14.
Liu et al., "Analysis of Serum Total and Free PSA Using Immunoaffinity Depletion Coupled to SRM: Correlation with Clinical Immunoassay Tests", Journal of Proteomics, 75, 2012, pp. 4747-4757.
Liu et al., "Evaluation of Multiprotein Immunoaffinity Subtraction for Plasma Proteomics and Candidate Biomarker Discovery Using Mass Spectrometry*", Molecular & Cellular Proteomics, 5, 2006, pp. 2167-2174.
Maclean et al., "Skyline: An Open Source Document Editor for Creating and Analyzing Targeted Proteomics Experiments", Bioinformatics, 26, 7, 2010, pp. 966-968.
Malmstrom et al., "Proteome-Wide Cellular Protein Concentrations of the Human Pathogen Leptospira Interrogans", Nature, 460, 2009, pp. 762-765.
McCormack et al., "Molecular Forms of Prostate-Specific Antigen and the Human Kallikrein Gene Family: A New Era", Urology, 45, 1995, 5, pp. 729-744.
Nicol et al., "Use of an Immunoaffinity-mass Spectrometry-based Approach for the Quantification of Protein Biomarkers from Serum Samples of Lung Cancer Patients*", Molecular & Cellular Proteomics, 7, 2008, pp. 1974-1982.
Petrovics et al., "Frequent Overexpression of ETS-related Gene-1 (ERG1) in Prostate Cancer Transcriptome", Oncogene, 24, 2005, pp. 3847-3852.
Picotti et al., "Full Dynamic Range Proteome Analysis of S. cerevisiae by Targeted Proteomics", Cell, 138, 2009, pp. 795-806.

(56) References Cited

OTHER PUBLICATIONS

Picotti et al., "Selected Reaction Monitoring-Based Proteomics: Workflows, Potential, Pitfalls and Future Directions", Nature Methods, vol. 109, No. 6, May 30, 2012 (May 30, 2012), pp. 555-566.
Prakash et al., "Expediting the Development of Targeted SRM Assays: Using Data from Shotgun Proteomics to Automate Method Development", Journal of Proteome Research, 8, 2009, pp. 2733-2739.
Prestigiacomo et al., "Clinical Usefulness of Free and Complexed PSA", Scand Journ. Clin Lab Invest. Suppl, 221, 1995, pp. 32-34.
Qian et al., "Enhanced Detection of Low Abundance Human Plasma Proteins Using a Tandem IgY12-SuperMix Immunoaffinity Separation Strategy*", Molecular & Cellular Proteomics, 7, 2008, pp. 1963-1973.
Rafferty et al., "Reference Reagents for Prostate-Specific Antigen (PSA): Establishment of the First International Standards for Free PSA and PSA (90:10)", Clinical chemistry, 46, 9, 2000, pp. 1310-1317.
Rezeli et al.,"Moving Towards High Density Clinical Signature Studies with a Human Proteome Catalogue Developing Multiplexing Mass Spectrometry Assay Panels", Journal of Clinical Bioinformatics, 2011, 1(7), pp. 1-9.
Rifai et al., "Protein Biomarker Discovery and Validation: The Long and Uncertain Path to Clinical Utility", Nature Biotechnology, 24, 8, 2006, pp. 971-983.
Semjonow et al., "Discordance of Assay Methods Creates Pitfalls for the Interpretation of Prostate-Specific Antigen Values", The Prostate Supplement, 7, 1996, pp. 3-16.
Shi et al., "Advancing the Sensitivity of Selected Reaction Monitoring-Based Targeted Quantitative Proteomics", Proteomics, 12, 2012, pp. 1074-1092.
Shi et al., "Antibody-Free, Targeted Mass-Spectrometric Approach for Quantification of Proteins at Low Picogram Per Milliliter Levels in Human Plasma/Serum", PNAS, vol. 109, No. 38, pp. 15395-15400 and SI Appendix S1-S75. Sep. 18, 2012 (Sep. 18, 2012), 81 pages.
Stahl-Zeng et al., "High Sensitivity Detection of Plasma Proteins by Multiple Reaction Monitoring of N-Glycosites*", Molecular & Cellular Proteomics, 6, 2007, pp. 1809-1817.
Tomlins et al., "Recurrent Fusion of TMPRSS2 and ETS Transcription Factor Genes in Prostate Cancer", Science, vol. 310, 2005, pp. 644-648.
Wang et al., "Mutant Proteins as Cancer-Specific Biomarkers", PNAS, 108, 6, Feb. 8, 2011, pp. 2444-2449.
Wang et al., "Reversed-Phase Chromatography with Multiple Fraction Concatenation Strategy for Proteome Profiling of Human MCF10A Cells", Proteomics, 11, 2011, pp. 2019-2026.
Whiteaker et al., "A Targeted Proteomics-Based Pipeline for Verification of Biomarkers in Plasma", Nature Biotechnology, 27, 7, 2011, pp. 625-634.
Whiteaker et al., "An Automated and Multiplexed Method for High Throughput Peptide Immunoaffinity Enrichment and Multiple Reaction Monitoring Mass Spectrometry-Based Quantification of Protein Biomarkers*", Molecular & Cellular Proteomics, 9, 2010, pp. 184-196.
Whiteaker et al., "Evaluation of Large Scale Quantitative Proteomic Assay Development Using Peptide Affinity-Based Mass Spectrometry*", Molecular & Cellular Proteomics, 10, M110.005645, 10 pages.
Wolf-Yadlin et al., "Multiple Reaction Monitoring for Robust Quantitative Proteomic Analysis of Cellular Signaling Networks", PNAS, 104, 14, Apr. 3, 2007, pp. 5860-5865.

* cited by examiner

SEQUENCE LISTING

<160> NUMBER OF SEQ ID NOS: 30

<210> SEQ ID NO 1
<211> LENGTH: 9
<212> TYPE: PRT

```
<213> ORGANISM: Bos Taurus

<400> SEQUENCE: 1

Asp Phe Pro Ile Ala Asn Gly Glu Arg
1               5

<210> SEQ ID NO 2
<211> LENGTH: 9
<212> TYPE: PRT
<213> ORGANISM: Bos Taurus

<400> SEQUENCE: 2

Asp Gly Pro Leu Thr Gly Thr Tyr Arg
1               5

<210> SEQ ID NO 3
<211> LENGTH: 10
<212> TYPE: PRT
<213> ORGANISM: Bos Taurus

<400> SEQUENCE: 3

Val Leu Val Leu Asp Thr Asp Tyr Lys Lys
1               5                   10

<210> SEQ ID NO 4
<211> LENGTH: 20
<212> TYPE: PRT
<213> ORGANISM: Bos Taurus

<400> SEQUENCE: 4

Val Tyr Val Glu Glu Leu Lys Pro Thr Pro Glu Gly Asp Leu Glu Ile
1               5                   10                  15

Leu Leu Gln Lys
            20

<210> SEQ ID NO 5
<211> LENGTH: 12
<212> TYPE: PRT
<213> ORGANISM: Escherichia coli

<400> SEQUENCE: 5

Val Asp Glu Asp Gln Pro Phe Pro Ala Val Pro Lys
1               5                   10

<210> SEQ ID NO 6
<211> LENGTH: 11
<212> TYPE: PRT
<213> ORGANISM: Escherichia coli

<400> SEQUENCE: 6

Leu Trp Ser Ala Glu Ile Pro Asn Leu Tyr Arg
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Sequence synthesized with carbamidomethyl
      cysteine

<400> SEQUENCE: 7

Ile Val Gly Gly Trp Glu Cys Glu Lys
1               5
```

<210> SEQ ID NO 8
<211> LENGTH: 12
<212> TYPE: PRT
<213> ORGANISM: Homo sapiens

<400> SEQUENCE: 8

Leu Ser Glu Pro Ala Glu Leu Thr Asp Ala Val Lys
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Isotopically labelled peptide constructed with
      13C and 15N on terminal amino acid.

<400> SEQUENCE: 9

Ala Gly Thr Phe Val Ala Ala Arg
1               5

<210> SEQ ID NO 10
<211> LENGTH: 8
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 10

Ser Asp Val Gly Ala Leu Leu Lys
1               5

<210> SEQ ID NO 11
<211> LENGTH: 8
<212> TYPE: PRT
<213> ORGANISM: Artificial Sequence
<220> FEATURE:
<223> OTHER INFORMATION: Peptide constructed with carbamidomethyl
      cysteine and isotopically labelled with 13C and 15N on terminal
      amino acid

<400> SEQUENCE: 11

Glu Leu Gly Pro Ser Pro Ile Lys
1               5

<210> SEQ ID NO 12
<211> LENGTH: 8
<212> TYPE: PRT
<213> ORGANISM: Artificial Sequence
<220> FEATURE:
<223> OTHER INFORMATION: Isotopically labelled peptide constructed wtih
      13C and 15N on terminal amino acid

<400> SEQUENCE: 12

Val Ser Ser Ile Ile Glu Pro Arg
1               5

<210> SEQ ID NO 13
<211> LENGTH: 8
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 13

```
Ile Val Ala Asp Glu Met Val Lys
1               5

<210> SEQ ID NO 14
<211> LENGTH: 9
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 14

Ala Leu Glu Ala Val Glu Ala Ala Arg
1               5

<210> SEQ ID NO 15
<211> LENGTH: 9
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 15

Val Asn Asp Ala Gly Ile Ile Glu Arg
1               5

<210> SEQ ID NO 16
<211> LENGTH: 9
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 16

Val Val Glu Val Ser Pro Thr Thr Arg
1               5

<210> SEQ ID NO 17
<211> LENGTH: 9
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 17

Asp Leu Glu Val Ile Ser Ser Gln Arg
1               5

<210> SEQ ID NO 18
<211> LENGTH: 10
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 18

Met Val Gly Thr Asn Pro Asp Thr Val Lys
1               5                   10

<210> SEQ ID NO 19
<211> LENGTH: 10
<212> TYPE: PRT
<213> ORGANISM: Artificial Sequence
<220> FEATURE:
```

```
<223> OTHER INFORMATION: Isotopically labelled peptide constructed with
      13C and 15N on terminal amino acid

<400> SEQUENCE: 19

Asp Asn Asp Asn Pro Phe Glu Leu Val Arg
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 20

Asn Ser Phe Pro Gly Asp Glu Ile Pro Ile Val Arg
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 21

Tyr Gln Gly Thr Pro Glu Asp Asn Leu Arg
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 22

Phe Glu Gly Ala Ala Thr Glu Thr Ser Tyr Glu Arg
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 23

Ala Gln Ile Glu Glu Thr Glu Ser Ala Phe Asp Arg
1               5                   10

<210> SEQ ID NO 24
<211> LENGTH: 19
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 24

Gly Ala Ala Pro Ala Ser Ala Ala Ala Ala Glu Glu Ala Pro Ala
1               5                   10                  15

Glu Asp Lys
```

```
<210> SEQ ID NO 25
<211> LENGTH: 13
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 25

Leu Tyr Thr Leu Thr Pro Glu Tyr Gly Ala Pro Gly Arg
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 26

Phe Glu Gly Ala Ala Thr Glu Thr Ser Tyr Glu Arg
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Isotopically labelled peptide constructed with
      13C and 15N on terminal amino acid

<400> SEQUENCE: 27

Ala Gln Ile Glu Glu Thr Glu Ser Ala Phe Asp Arg
1               5                   10

<210> SEQ ID NO 28
<211> LENGTH: 21
<212> TYPE: PRT
<213> ORGANISM: Homo sapiens

<400> SEQUENCE: 28

Asn Thr Gly Gly Ala Ala Phe Ile Phe Pro Asn Thr Ser Val Tyr Pro
1               5                   10                  15

Glu Ala Thr Gln Arg
            20

<210> SEQ ID NO 29
<211> LENGTH: 21
<212> TYPE: PRT
<213> ORGANISM: Homo sapiens

<400> SEQUENCE: 29

Phe Asp Phe His Gly Ile Ala Gln Ala Leu Gln Pro His Pro Pro Glu
1               5                   10                  15

Ser Ser Leu Tyr Lys
            20

<210> SEQ ID NO 30
<211> LENGTH: 27
<212> TYPE: PRT
<213> ORGANISM: Artificial Sequence
<220> FEATURE:
<223> OTHER INFORMATION: Isotopically labelled peptide constructed with
      13C and 15N on terminal amino acid
```

```
<400> SEQUENCE: 30

Leu Ala Asn Pro Gly Ser Gly Gln Phe His Gly Ile Ala Gln Ala Leu
1               5                   10                  15

Gln Pro His Pro Pro Glu Ser Ser Leu Tyr Lys
            20                  25
```

PROCESS FOR ULTRA-SENSITIVE QUANTIFICATION OF TARGET ANALYTES IN COMPLEX BIOLOGICAL SYSTEMS

CROSS-REFERENCE TO RELATED APPLICATIONS

The present application is a continuation of U.S. patent application Ser. No. 13/736,279 filed on 8 Jan. 2013, which is hereby incorporated by reference in its entirety. Further, the corresponding published application U.S. Patent Application Publication Number US 2014/0194304 A1 published 10 Jul. 2014, is hereby incorporated by reference in its entirety.

STATEMENT REGARDING RIGHTS TO INVENTION MADE UNDER FEDERALLY-SPONSORED RESEARCH AND DEVELOPMENT

This invention was made with Government support under the National Institutes of Health (NIH) Director's New Innovator Program Award Number DP2OD006668, NIH Grant Numbers 8P41-GM103493, 5P41-RR018522, CA111244, and U24-CA-160019, National Cancer Institute (NCI) Early Detection Research Network Interagency Agreement Number Y01-CN-05013-29, and Contract Number DE-ACO5-76RLO-1830 awarded by the U.S. Department of Energy. The Government has certain rights in the invention.

FIELD OF THE INVENTION

The present invention relates generally to analytical separation and measurement systems and processes. More particularly, the present invention relates to two-dimensional separation systems and processes that quantify low-abundance target analytes in complex samples including complex biological and clinical samples.

BACKGROUND OF THE INVENTION

Detection and quantification of trace levels of target proteins in complex biological systems are of critical importance for verification and validation of candidate biomarkers in biomedical research and in the profiling of cellular signaling pathways in systems biology studies. The term "complex" as used herein refers to samples that contain so many components that low-abundance components of interest cannot be adequately and/or directly separated, resolved, detected, and/or quantified without additional and/or rigorous processing. For example, sensitive detection of low-abundance proteins in complex biological samples has typically been achieved using immunoassays that employ antibodies specific to the target proteins. However, de novo development of specific antibodies for new immunoassays is costly, requires long development lead times, and often experiences high failure rates.

Selected Reaction Monitoring (SRM), also known as Multiple Reaction Monitoring (MRM), has recently emerged as a promising technology for high-throughput mass spectrometry (MS)-based quantification of target proteins in biological and clinical specimens (e.g., tumor tissues). While SRM has demonstrated relatively good selectivity, reproducibility or precision, and sensitivity for a range of multiplexed protein assays, a major limitation of current SRM technology is insufficient sensitivity for detecting very low-abundance compounds including, e.g., proteins present at sub-nanogram per milliliter levels in human blood plasma or serum samples, or extremely low-abundance proteins in cells or tissues. To date, without sample pre-fractionation, liquid chromatography (LC)-SRM measurements have been limited to only moderately abundant proteins in the low microgram per milliliter range.

More recently, the combination of immunoaffinity depletion and fractionation by Strong Cation Exchange (SCX) Chromatography, along with advances in MS sensitivity, has extended SRM quantification of plasma proteins to low nanogram per milliliter levels. Stable Isotope Standards and Capture by Anti-Peptide Antibodies (SISCAPA) coupled with SRM has demonstrated quantification of target proteins in the same range using as little as 10 µL of human plasma. SISCAPA assays have some distinct advantages over conventional immunoassays in terms of assay development and specificity, and offer sensitivity for low nanogram per milliliter detection of plasma proteins. However, despite these advances, antibody-specific reagents that have sufficient specificity for target proteins such as protein isoforms, post-translational modifications, or their surrogate (native) peptides are generally not available, and development of such reagents is expensive and requires a long lead time. Accordingly, new approaches are needed that quantify trace quantities of important biological targets. The present invention addresses these needs.

SUMMARY OF THE INVENTION

Processes are disclosed for quantifying very low abundance target analytes derived from highly complex biological samples present in individual or groups of fractions obtained from a separation stream including, e.g., biological fluids, cells, and/or tissues. The process does not require specific affinity-based reagents as required in the conventional art for measurements involving, e.g., very low-abundance proteins.

The process may include intelligently selecting one or more fractions from the separation stream in real time which contain a selected internal standard or marker, or fractions that match a metric selective or predictive for the low-abundance target analytes of interest.

The process may include analyzing one or more of the intelligently selected fractions to quantify the low-abundance target analytes present in the intelligently selected fractions. One or more of the process steps of the method may be automated.

Target analytes may include, but are not limited to, e.g., proteins, peptides, modified proteins (e.g., post-translational modified proteins), mutated proteins, protein biomarkers, signaling proteins, drugs, metabolites, lipids, antibodies, viruses, and other compounds present in biofluid, cell, and/or tissue samples. Other complex samples may also be analyzed including complex environmental samples.

The process may include binning one or more intelligently selected fractions into individual bins or sample wells. Binning may include introducing individual fractions into a collection plate or a multidimensional array containing any number (N) of collection wells or bins. Number of bins or wells is not limited. The binning may include sorting intelligently selected fractions with different elution times into individual bins or collection wells as the fractions elute from a separations device.

Intelligent selection may include detecting an SRM signal of an internal standard that includes an isotopically-labeled heavy isotope introduced into the sample that is present in the intelligently selected fractions from the process stream in real time and binning those intelligently selected fractions into individual bins or wells. Intelligent selection may include separating fractions from the process stream in concert with a high-resolution separation process. Separation processes include, but are not limited to, e.g., reversed-phase liquid chromatography, hydrophilic interaction chromatography, electrostatic repulsion hydrophilic interaction chromatography, capillary electrophoresis, other separation processes, and combinations of these various separation approaches.

Intelligently selecting fractions from the separation stream can include monitoring at least a portion of the fractions on-line or off-line to identify those fractions containing a selected internal standard or marker. In some applications, fast off-line LC-SRM screening can be used to screen individual fractions. Selecting fractions may also include identifying fractions in the separation stream that match a metric that is predictive of or that is otherwise selective for low-abundance target analytes of interest in the fractions. For example, fractions may be selected that have an elution time (i.e., the metric) that matches with that of a low-abundance target analyte of interest therein. Selecting fractions may also include discarding fractions from the separation stream that do not include the selected internal standard or that do not match with the selected metric.

Selecting fractions may include multiplexing one or more of the intelligently selected fractions to concentrate target analytes of interest therein.

Analyzing selected fractions may include multiplexing one or more of the intelligently selected fractions prior to analyzing the fractions.

Multiplexing may include combining one or more intelligently selected fractions having different elution times to provide sufficient peak separation during a subsequent SRM analysis. Multiplexing may include combining between four and twelve intelligently selected fractions prior to analyzing the fractions. Multiplexing may also include combining between ten and 100 intelligently selected fractions prior to analyzing the fractions. Multiplexing may include combining between 100 and 500 intelligently selected fractions prior to analyzing the fractions.

Since chromatographic fractionation is reproducible for samples of a given type from sample to sample, one need only screen all of the fractions obtained from one selected sample to determine which target fractions need to be selected for all remaining samples. Monitoring fractions may be performed on-line or off-line. For example, monitoring may include analyzing a portion of individual fractions from one sample with, e.g., a mass-selective instrument, a UV detection device (e.g., with UV detection monitoring), with on-line SRM monitoring, with rapid off-line LC-SRM monitoring, or other monitoring approaches. As an example, off-line LC-SRM screening of internal standards can be performed using fast LC separations that provide a separation time of under 1 minute per fraction. However, monitoring approaches are not intended to be limited to these selected approaches.

Quantifying target analytes may include multiplexing two or more of the intelligently selected fractions to increase overall sample throughput prior to SRM analysis without sacrificing overall sensitivity. And, the number of fractions that can be effectively combined increases in approximate proportion to the total number of first dimension fractions obtained. For example, in some applications, up to eight fractions that have different elution times may be combined to increase overall sample throughput prior to SRM analysis without sacrificing overall sensitivity.

A process is also disclosed for quantifying low-abundance target analytes present in individual, and groups of, fractions in a separation stream derived from a complex sample including, e.g., biological fluids, cells, and/or tissues. The process may include a first dimension analysis and a second dimension analysis. The first dimension analysis may include: fractionating the complex sample to form one or more individual fractions containing potential low-abundance target analytes of interest therein; separating the one or more individual fractions from the process stream; intelligently selecting one or more individual fractions from the process stream in real time containing a selected internal standard, marker, or matching a metric selective or predictive for the low-abundance target analytes of interest therein. Depleting high-abundance components from the sample to concentrate low-abundance target analytes of interest in the remaining sample may be incorporated into the first dimension analysis to further enhance SRM sensitivity and quantitation accuracy.

First dimension separation may include fractionating (separating) the sample to provide individual fractions in a flowing process stream containing one or more potential target analytes of interest therein. The fractions may include heavy internal standards that are spiked into the sample. Individual fractions in the process stream may be monitored on-line in real time (e.g., with SRM monitoring) or monitored off-line to identify fractions in the process stream containing the internal standard or those fractions that match a metric (e.g., an elution time metric) that is selective for low-abundance target analytes of interest. The first dimension analysis may further include intelligently selecting fractions from the process stream containing the selected internal standard, marker, or those that match the metric selective for the low-abundance target analytes of interest. Intelligently selected fractions may be placed into individual bins or wells to concentrate the low-abundance target analytes therein. Individual fractions may also be combined or multiplexed to concentrate the low-abundance target analytes therein. Intelligently selecting first-dimension sample fractions from the process stream may include detecting or identifying heavy labeled internal standards present in the fractions via on-line SRM monitoring. Selecting first-dimension sample fractions from the process stream may also be based on metrics such as elution times that are selective or predictive for target analytes of interest in the sample fractions. Second dimension analysis may include analyzing one or more of the intelligently selected fractions to quantify low-abundance target analytes in the fractions at a sufficient level of sensitivity.

Further aspects of the present invention are detailed in a publication (citing supplemental data) by Shi et al. (Proceedings of the National Academy of Sciences of the United States of America (PNAS), Sep. 18, 2012, Vol. 109, No. 38, pgs. 15395-15400), which reference is incorporated herein in its entirety.

The purpose of the foregoing abstract is to enable the U.S. patent and Trademark Office and the public generally, especially scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way. Various advantages and novel features of the present invention are described herein and will become further readily apparent to those skilled in this art from the following detailed description. In the preceding and following descriptions the preferred embodiment of the invention is shown and described by way of illustration of the best mode contemplated for carrying out the invention. As will be realized, the invention is capable of modification in various respects without departing from the invention. Accordingly, drawings and descriptions of the preferred embodiment set forth hereafter are to be regarded as illustrative in nature, and not as restrictive. A more complete appreciation of the invention will be readily obtained by reference to the following description of the accompanying drawings in which like numerals in different figures represent the same structures or elements.

DETAILED DESCRIPTION OF THE INVENTION

Figure 1A:
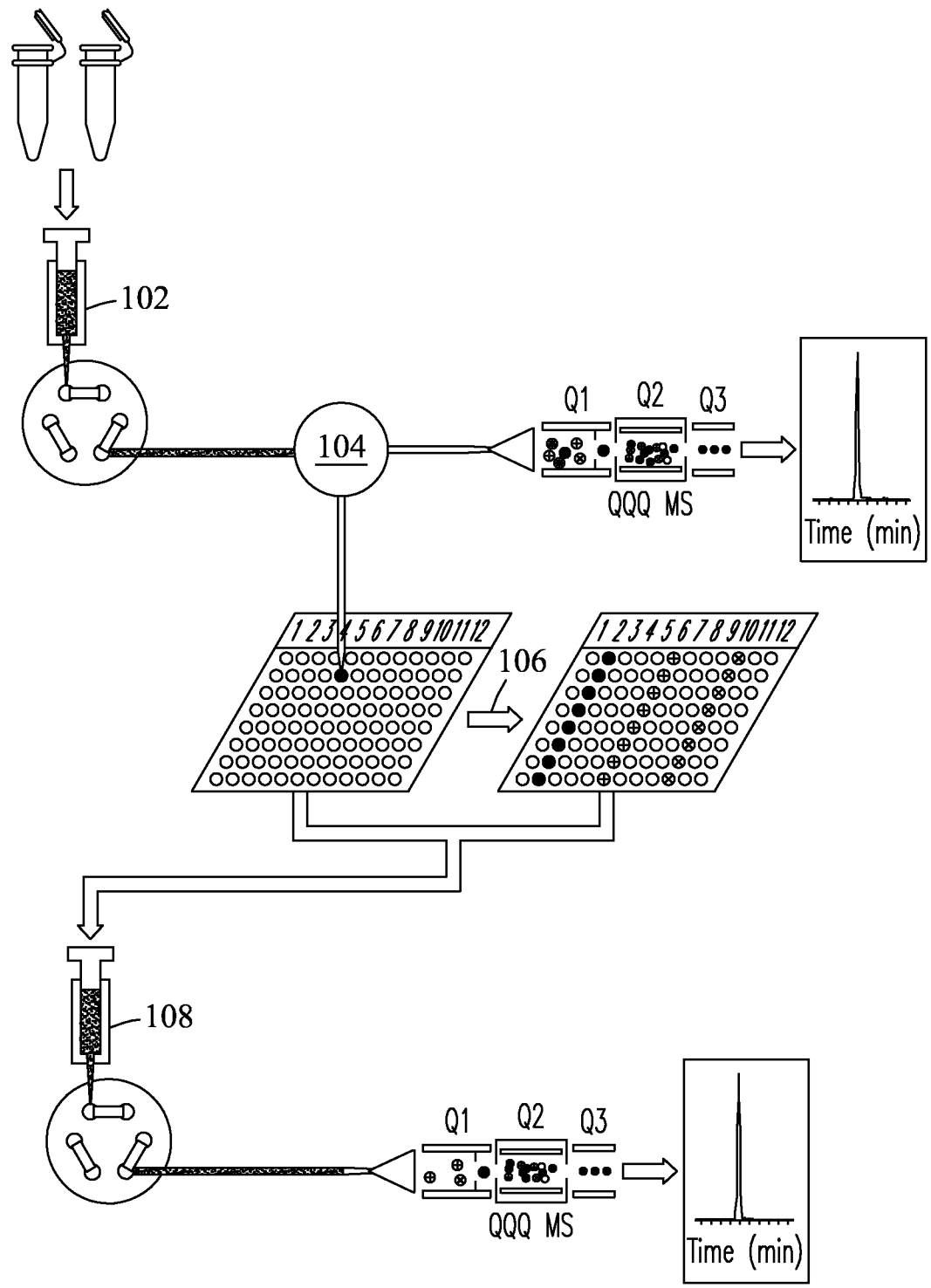
FIGS. 1a-1b show exemplary processes according to different embodiments of the present invention.

New processes are disclosed that provide ultra-sensitive quantification of low-abundance target analytes in complex samples such as human blood plasma and blood serum samples. The term "ultra-sensitive" means quantification of low-abundance target analytes in concert with immunoaffinity depletion in sample fractions at concentrations less than or equal to about 50 pg/mL (≤~50 pg/mL), or quantification of low-abundance target analytes without affinity reagent support at concentrations less than or equal to about 1 ng/mL.

The process may include two dimensions of sample separation and subsequent quantification termed PRISM-SRM involving high-pressure (P), high-resolution (R) separations, intelligent selection (IS), multiplexing (M) (termed "PRISM"), and quantification involving Selected Reaction Monitoring (SRM). The following description includes a best mode of one embodiment of the present invention. It will be clear from this description of the invention that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood that there is no intention to limit the invention to the specific form disclosed, but, on the contrary, the invention covers all modifications, alternative constructions, and equivalents falling within the scope of the invention as defined in the claims.

Sample Preparation

A sample containing biological analytes of interest may be prepared for analysis in concert with the present invention by digesting proteins (e.g., as a tryptic digest) in the sample to form peptides of a selected size. Proteins may be digested with, e.g., an enzyme or, more particularly, a serine protease such as trypsin that hydrolyzes proteins by cleaving peptide chains at the carboxyl side of the amino acids lysine and arginine. Digestion can yield a tryptic digest containing a mixture of peptides of various sizes, including low-abundance peptides of interest. Enzyme digestion of proteins may be performed to generate peptides with a molecular weight between about 500 Daltons (Da) and about 4000 Daltons (Da). Peptides with molecular weights in this range are sufficiently small that they effectively fragment producing fragments that are smaller than the parent (or precursor) ions when colliding with a collision gas in a mass spectrometer (e.g., during SRM monitoring).

Sample preparation may further include spiking the digested sample with so-called "heavy" labeled peptides. Digestion and/or spiking can prepare the sample for peptide fractionation described hereafter. In exemplary tests described herein, tryptic digests of four target proteins containing, e.g., bovine carbonic anhydrase, bovine β-lactoglobulin, E-coli β-galactosidase, and human prostate-specific antigen (PSA) obtained commercially [Sigma-Aldrich, St. Louis, Mo., USA] were spiked into human female plasma digests [BioChemed, Winchester, Va., USA] at protein concentrations ranging from 50 pg/mL to 100 ng/mL. In some embodiments, samples may be prepared for first dimension fractionation by depleting the samples of high-abundance components (e.g., using IgY14-depletion). FIG. 1b discussed further herein shows an exemplary IgY14-PRISM-SRM process for quantifying low-abundance target analytes, e.g., in human blood samples in accordance with the present invention, but the invention is not intended to be limited to analysis of depleted samples.

Internal Standards

Internal standards include, but are not limited to, heavy isotope-labeled surrogates. The term "heavy isotope-labeled" surrogate refers to an isotope-labeled reference, standard, or peptide that replaces common isotopes such as $^{12}C$ and $^{14}N$ in the molecule with heavier signal-generating isotopes such as $^{13}C$ or $^{15}N$. These standards thus include a molecular weight that is greater than the corresponding unlabeled surrogate (i.e., native, endogenous, or "light") peptide. Samples (e.g., tryptic digests) may be spiked with an internal standard (e.g., a surrogate peptide) [termed "stable isotope dilution (SID)] that signals the presence of low-abundance targets of interest in various fractions present in a sample stream, or those that elute with a target analyte of interest. Accurate elution profiles of internal standards allow precise determination of expected elution times or locations, e.g., for separation of target fractions that include the target analytes (e.g., peptides) of interest. Internal standards are preferred that have the same or similar chemical properties as the target analytes of interest.

In exemplary tests performed herein, internal standards for four target proteins included synthetic heavy peptides obtained commercially (Thermo Fisher Scientific, San Jose, Calif., USA) that were labeled with $^{13}C$ and $^{15}N$ on C-terminal lysine and arginine.

Prism-SRM

1$^{st}$ Dimension Separation and Analysis

Figure 1B:
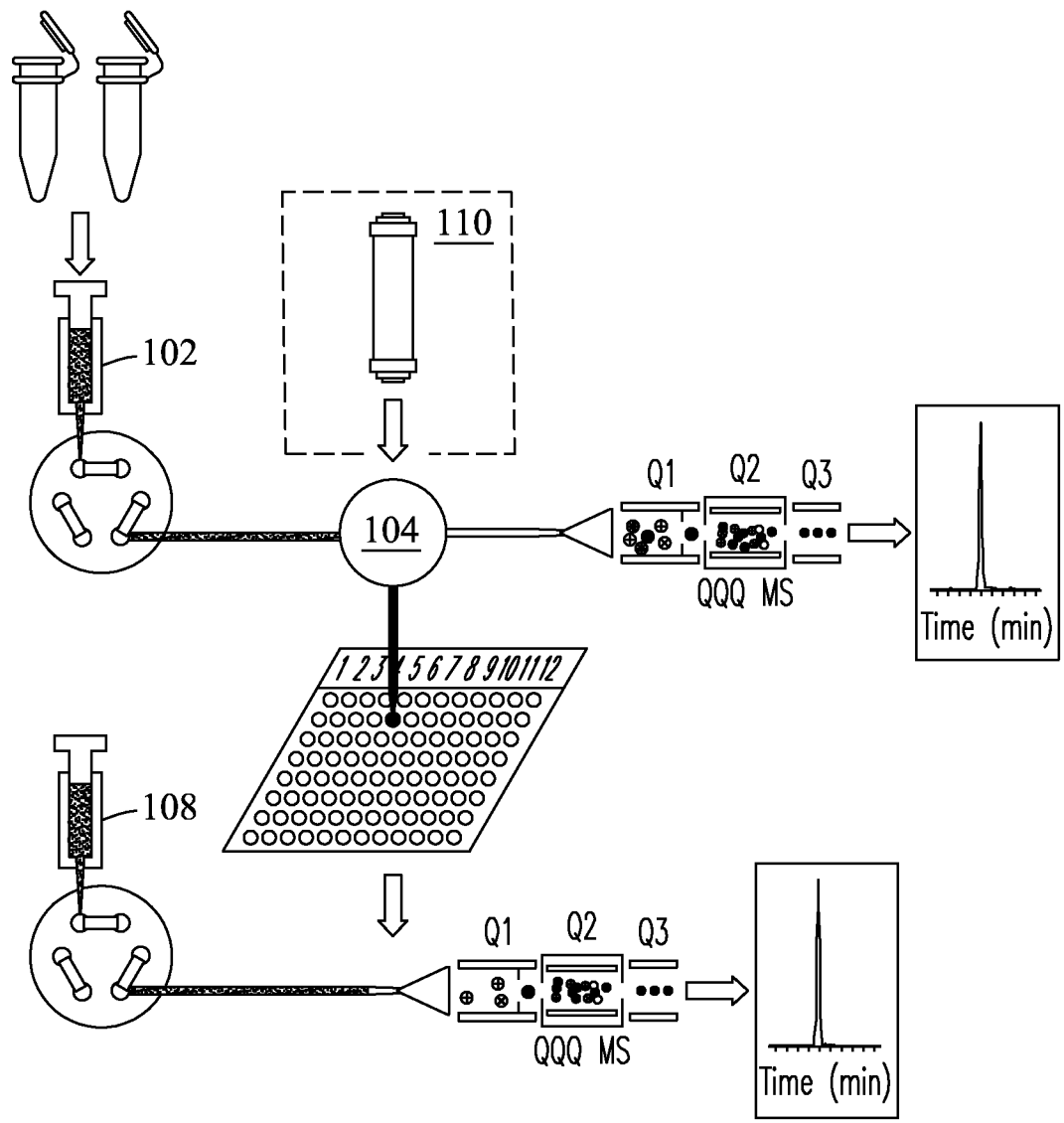

FIG. 1a shows a PRISM-SRM (two dimension) process 100 of the present invention that includes a first dimension fractionation (separation) and selection of sample fractions containing low-abundance target analytes of interest and a second dimension separation and quantification of low-abundance targets. The term "first dimension" refers to any of the one or more process steps performed to fractionate (separate), monitor, select, and/or multiplex target fractions prior to quantifying low-abundance targets of interest, as detailed hereafter. The term "second dimension" refers to any of the one or more process steps performed after separation and selection that quantifies low-abundance target analytes of interest in individual or multiplexed fractions, as detailed hereafter. While the process is described in reference to a plasma or serum sample, the process is not intended to be limited to any one sample type. In addition, the process is not intended to be limited to a specific order of steps, as will be illustrated herein. For example, as detailed hereafter, the PRISM-SRM process may include a first dimension fractionation (separation) of fractions in a separation stream, intelligent selection (termed i-selection) of individual fractions into individual wells or multiplexing (i.e., combining) of individual fractions in order to enhance SRM sensitivity. The term "fraction" used herein refers to a portion, a part, a volume, or a quantity of a larger whole. As an example, a fraction may contain, e.g., target analytes such as peptides collected from a larger complexed polypeptide-containing sample that can provide useful information for peptide sequencing, protein identification, and quantification. Thus, no limitation to any specific sequence or to any single set of steps is intended. For example, other pre-fractionation strategies, such as immunoaffinity depletion that removes high-abundance target analytes may be incorporated into PRISM-SRM to further enhance PRISM-SRM sensitivity.

Sample Fractionation

In one step (102) of the present invention, a sample (e.g., a human blood sample) may be fractionated (separated) into one or more individual fractions that contain a potential analyte therein. In a preferred embodiment, fractionation may include separating peptides in a sample or a tryptic digest sample into one or more fractions for collection into individual wells. Separation of fractions may be performed with, e.g., high resolution reversed-phase liquid chromatography (LC), hydrophilic interaction chromatography, electrostatic repulsion-hydrophilic interaction chromatography, like processes, including combinations of these various high-resolution separation approaches. As an example, fractionation may include loading peptides in a tryptic digest sample containing spiked internal standards onto a LC column and separating the peptides from the separation stream into individual sample fractions (e.g., 96 fractions) containing individual peptides into different wells.

High-resolution reversed-phase capillary LC (or cLC) is a preferred separation approach as it provides maximum resolution and reproducible separations of sample fractions compared with conventional approaches such as Strong Cation Exchange (SCX) chromatography. For example, conventional SCX fractionation involves salt-gradient elution which typically requires additional clean-up steps to remove salts used in the process. In contrast, cLC enrichment purifies sample fractions such that they are compatible with downstream LC-MS analyses without the need for additional cleanup or removal of interfering matrix components.

PRISM can provide separation of individual fractions from the separation stream using, e.g., high resolution, reversed phase separations. The term "high resolution" means fractions separated from the separation stream may contain a single target analyte or may contain one or more target analytes with a single elution time. The process reduces the complexity of a sample such that, following fractionation, a given target analyte may reside in a single fraction and be absent from another fraction. For example, high-resolution separations can separate and isolate a first individual fraction from a next individual fragment, or provide fractions that exhibit different elution profiles. High-resolution separations may employ high pH (i.e., pH≥10) mobile phases that serve to enrich (concentrate) the target analytes prior to their quantification. "Enrichment" as used herein refers to steps that isolate, concentrate, and purify target analytes of interest from other analytes and matrix interferences in the sample. For example, high-resolution separation of peptide mixtures effectively separates target peptides from other peptides in the sample. Such separations for individual fractions also yield chromatograms in which the chromatographic (i.e., LC) peaks are resolved. Resolution of one peak from another peak in the separation process maximizes the purity, and thus the concentration, of the target analyte of interest. Maximum enrichment of the target analyte of interest may be achieved by maximizing the quantity of sample collected corresponding to the IS signal while monitoring the SRM signal of the internal standard. For example, separation of one peptide from another peptide in the sample stream provides a single sample component that maximizes the sensitivity obtained in the quantifying analysis.

Drugs and metabolites can also be separated, e.g., in a reversed phase LC column. For example, in some embodiments, separation may be performed with, e.g., high resolution, reversed-phase capillary LC (e.g., 200 μm i.d.×50 cm length) systems employing a high pH (e.g., pH 10) mobile phase, or another separation method.

Number of fractions is not limited. Number of fractions obtained depends in part on the number of target analytes, physical properties (e.g., orthogonality) of the analytes, size of analytes within the parent sample, and other selected physical properties as will be understood by those of ordinary skill in the art. No limitations are intended.

i-Selection and SRM Monitoring

In another step (104), PRISM-SRM may involve intelligently selecting (termed i-Selection) fractions in the separation stream in real time containing potential analytes (e.g., peptides) of interest. Intelligent selection may involve identifying fractions containing, e.g., an internal standard or other selected marker spiked into the original sample prior to fractionation. Internal standards present within target fractions may be monitored, e.g., via on-line SRM monitoring, UV detection monitoring, or fast off-line screening (e.g., ≤1 minute per fraction), as detailed herein. A selected metric (e.g., elution time) that is predictive for low-abundance target analytes of interest may also be used to intelligently select the fractions of interest.

In some embodiments, i-Selection of target fractions may involve intelligence derived from on-line SRM monitoring and detection of internal standards in real time, or separation metrics that provide sufficient evidence that the target material may be present in the selected fraction(s), to accurately locate and select target peptide fractions for quantification, but the invention is not intended to be limited thereto. For example, other strategies may be used to pinpoint target fractions including, but not limited to, e.g., off-line determination of the locations of target fractions and relying on the reproducibility of HPLC to locate target fractions from subsequent experiments. In addition, a limited number of target fractions eluted at different times during the first-dimension separation can also be multiplexed as described herein before performing the nano LC-SRM analysis to enhance sample throughput.

Intelligently selected fractions may then be collected as individual sample fractions from the separation stream, e.g., in a collection plate or a dimensional array containing any number (N) of wells including, e.g., 96 wells, 384 wells, or a plate or array containing a larger number of wells. Number of wells is not limited. i-Selection may thus be used to separate originally formed peptide mixtures into different bins for further analysis. SRM and/or UV monitoring can provide detection of internal standards and/or selection of peptide fractions based on expected elution times of target analytes of interest. Internal standards may include, but are not limited to, e.g., one or more synthetic peptides that are labeled with a heavy-isotope. Accurate elution profiles of internal standards allow precise determination of expected elution times for target peptides delivered into the collection plate or dimensional array. This process intelligently selects the most informative target fractions for downstream nano-LC-SRM measurements. Intelligent selection addresses drawbacks of conventional fractionation strategies that require analysis of complete and/or unnecessary fractions per sample.

i-Selection of target fractions can be advantageous in that it selects only those fractions that are likely to contain potential target analytes of interest and rejects those that do not. For example, accurate elution profiles of internal standards can allow precise determination of elution times and thus locations of target peptides of interest that may then be introduced into the collection plate. I-Selection can eliminate need to analyze non-identified or non-targeted fractions. Thus, i-Selection selects the most informative target fractions for downstream LC-SRM measurements (e.g., nano LC-SRM). As detailed hereinabove, number of sample fractions collected is not limited. In exemplary tests conducted herein, a 96-well plate was employed. But the approach can easily accommodate collection wells in excess of 100, 200, 300, 400, or more, including multi-dimensional wells. Thus, no limitations are intended. The steps of separation and i-Selection performed within the PRISM process can allow target analytes to be effectively separated, selected, and subsequently isolated in selected bins of interest for further analysis, as detailed hereafter.

Multiplexing

In an optional step (106), intelligently selected (i.e., i-Selected) fractions may be pooled or multiplexed for subsequent LC-SRM analysis. Multiplexing (or concatenation) of fractions may be performed prior to LC-SRM quantification for detection and quantification of trace levels of a wide range of targets in complex biological systems. "Multiplexing" as the term is used herein means to combine two or more individually selected fractions together to reduce the total number of fractions needing analysis.

The multiplexing strategy is based on the observation that the first dimension of separation and the second dimension of separation are partially orthogonal. "Orthogonality" is a relative assessment of how different the two dimensions of separations are. For example, if both dimensions are fully orthogonal (i.e., completely different), any sample fraction obtained from a first dimension of separation will occupy the entire separation space of a $2^{nd}$ dimension of separation, meaning that retention times between the first dimension of separation and the $2^{nd}$ dimension of separation will be uncorrelated. The present invention does not require fully orthogonal separations. Multiplexing of the present invention employs the inherent partial orthogonality that exists between the first dimension of separation and the second dimension of separation to increase overall sample throughput for analysis of selected fractions. As an example, high pH ($\geq 10$) and low pH ($\leq 3$) reversed-phase LC separations are partially orthogonal (i.e., exhibit from 10% to 20% orthogonality). Thus, in a given fraction, the first dimension of separation may occupy typically from about 10% to about 20% of the separation space in the $2^{nd}$ dimension. Therefore, fractions that elute, e.g., at early, middle, and late retention times may have little overlap in their elution profiles during the second-dimension LC separation and, thus, can be effectively multiplexed (combined) before performing LC-SRM.

A general rule for multiplexing fractions may be employed. Individual fractions having sufficiently large differences in respective LC retention times may be multiplexed (i.e., combined or pooled) provided elution profiles during the second-dimension LC separation are also resolved (i.e., have minimal overlap). The term "minimal overlap" means resolution of peaks in the combined or pooled fractions is sufficiently resolved to provide sufficient purity for sensitive detection of the analytes in the $2^{nd}$ dimension quantification detailed hereafter.

Quantification Analysis $2^{nd}$ Dimension Separation and Analysis

In another step (108), analytes present within individual target fractions of interest can be quantified, e.g., by direct downstream analysis using LC-SRM (e.g., nano LC-SRM) or may be analyzed after multiplexing selected fractions together, as detailed hereinabove. Quantification of low-abundance target analytes in concert with SRM coupled with addition of internal standards [stable isotope dilution (SID)] represents a true quantitative technique due to its selectivity, accuracy, and precision for target quantification, as detailed further herein. The process can reliably quantify low-abundance proteins at sub-nanogram or low (<100 pg/mL) picogram per milliliter quantities in plasma and serum samples, including e.g., prostate-specific antigen (PSA) in clinical serum samples, and low-abundance proteins that have a high correlation ($R^2 > 0.99$) with results obtained from Enzyme Linked Immunosorbent Assays (ELISA).

SRM exploits the unique capability of the triple quadrupole mass spectrometer for quantitative analyses. In SRM mode, there are two stages of mass selection. A mass of the intact targeted analyte (precursor ion) may be selected in the first quadrupole (Q1). In the second quadrupole (Q2), following fragmentation of the Q1 mass-selected precursor ion by collision-induced dissociation, a desired fragment or "transition" (i.e., product ion) may be selected in the third quadrupole (Q3), which is then transmitted to the detector. The term "transition" as used herein refers to a specific product ion selected from a specific precursor each with specific m/z values. In the second stage, instead of obtaining full scan MS/MS, where all the possible fragment ions derived from the precursor are mass analyzed in Q3, only a small number of transition ions are mass analyzed in the Q3. Quantitative measurements are based on the intensity profile of each transition recorded by the MS detector. The two stages of mass selection with unit mass resolution result in high selectivity by excluding most co-eluting interferences effectively. SRM scans individual transitions having narrow mass windows (i.e., 0.002 Da). Targeted MS analyses enhance the sensitivity for detection of peptides by up to two orders of magnitude (as compared to full MS/MS scans) by allowing rapid and continuous monitoring of specific ions of interest.

Sample Depletion

In an optional step (110), a sample may be depleted of, or otherwise partitioned from, high-abundance components such as high-abundance proteins (HAPs) that can block detection and quantification of low-abundance targets including, e.g., low-abundance proteins (or LAPs) of interest. The term "high-abundance" as used herein refers to components in the sample having a concentration in the sample ranging from micrograms per milliliter ($\geq\mu g/mL$) at the low end of the concentration range to milligrams per milliliter (mg/mL) at the high end of the concentration range. The term "low-abundance" as used herein refers to target analytes with a concentration less than or equal to nanograms per milliliter ($\leq ng/mL$). The difference in concentration between low-abundance targets and high-abundance sample components may be up to 10 orders of magnitude by comparison. As an example, depletion of HAPs may be performed, e.g., by passing the sample through an IgY14 immunoaffinity column that removes or depletes 14 specific HAPs from a sample. Depletion of high-abundance components decreases the wide dynamic range of concentrations in the sample (e.g., plasma), so that the concentration of low-abundance analytes (e.g., proteins) in the sample may be accurately determined and quantified. As an example, removal of HAPs from a sample can decrease the overall concentration of plasma proteins by up to 20-times, allowing a greater quantity of target peptides to be loaded onto a capillary liquid chromatography (cLC) column for sample fractionation (separation). For less complex samples such as urine, tissues, cells, and like systems, immunoaffinity depletion may not be required because sufficient loading of target analytes onto the cLC column can be achieved for high-resolution separation.

LC-SRM

FIG. 1b shows a second dimension LC-SRM separation and analysis process for quantifying low-abundance target analytes in fractions selected via i-Selection. As detailed above, the present invention minimizes background interferences via sample enrichment, which allows highly sensitive SRM quantification of low-abundance target analytes including, e.g., low-abundance proteins in human plasma/serum samples and trace quantities of other analytes. For example, following i-Selection, individual fractions of interest can be directly analyzed using LC-SRM (e.g., nano-LC-SRM) or can be multiplexed with other target-containing fractions and then analyzed using LC-SRM. Fractions may be analyzed individually or can be multiplexed prior to SRM quantification, as detailed hereafter.

Sample Size

Sample sizes may vary. For example, sample size in a typical direct nano-LC-SRM analysis without PRISM may be about 1 μg of total peptides. SRM sensitivity may be assessed based on the Limit of Detection (LOD) value and/or the Limit of Quantification (LOQ) value. Target fractions may be either directly subjected to nano-LC-SRM with, e.g., 4 μL of sample per injection (~45 ng of peptides on the nano-LC column) or multiplexed with other target fractions, e.g., with a final volume of 20 μL before nano-LC-SRM analysis.

Analytes

The present invention can detect and determine low-abundance target analyte compounds in complex biological samples and systems including, but not limited to, e.g., proteins, peptides, modified proteins (e.g., post-translational modified proteins), mutated proteins, protein biomarkers, signaling proteins (e.g., single-digit copies in cells or tissues), drugs, metabolites, lipids, antibodies, viruses, and other compounds present in, e.g., biofluids, cell, and/or tissue samples. All analytes that can be separated with, e.g., high-resolution liquid chromatography are within the scope of the invention. No limitations are intended.

Sensitivity of PRISM-SRM Assays

Sensitivity, reproducibility, precision, and accuracy of SRM assays for quantification of target analytes may be evaluated by comparing SRM signals obtained in standard LC-SRM analyses of the same samples. SRM sensitivities of the present invention with PRISM detection (e.g., using volumes as low as 15 μL of human blood) at concentrations of ~100 pg/mL are comparable to LC-SRM sensitivities reported to date for antibody-based approaches (e.g., SIS-CAPA) that require starting volumes of plasma as large as 1 mL. PRISM-SRM has also been shown to enable detection and quantification of PSA in non-depleted serum samples at analyte concentrations below nanograms per milliliter, with sample volumes as low as 2 μL. Furthermore, the approach also allows detection and quantification of protein isoforms in cancer cell lines, which are not quantifiable using standard SRM. PRISM-SRM has also demonstrated sufficient sensitivity when applied to cell or tissue samples to enable quantification of low-abundance proteins expressed at a concentration of single-digit protein copies per cell. Even with limited fraction concatenation, moderate throughput (e.g., 50 sample analyses per week depending upon experimental details) can be achieved. For example, when quantifying a relatively large number of proteins (i.e., 100), all 96 fractions may contain target peptides; however, these fractions can still be carefully combined into 12 multiplexed fractions based on peptide elution times to achieve moderate throughput.

Precision of PRISM-SRM Assays

Precision may be calculated using the Coefficient of Variation (CV) value expressed as a percentage, described hereafter. Coefficient of Variation (CV) as used herein is defined as the standard derivation (SD) divided by the mean. For PRISM-SRM measurements at the peptide level herein, for example, calculation for the 1 ng/mL concentration point involved three processing replicates. Mean value of the three processing replicates was obtained from three average L/H area ratio values. Each average L/H value was based on three technical replicates per processing replicate. Standard deviation was then calculated from the three average L/H values and their mean value. For other concentration points at the peptide level, CV calculation may be based on three technical replicates obtained from the LC-SRM measurements. For PSA protein-levels described herein, CV values were calculated as described for the 1 ng/mL concentrations hereinabove.

Quantification with Peptide Level Calibration

Figure 2A:
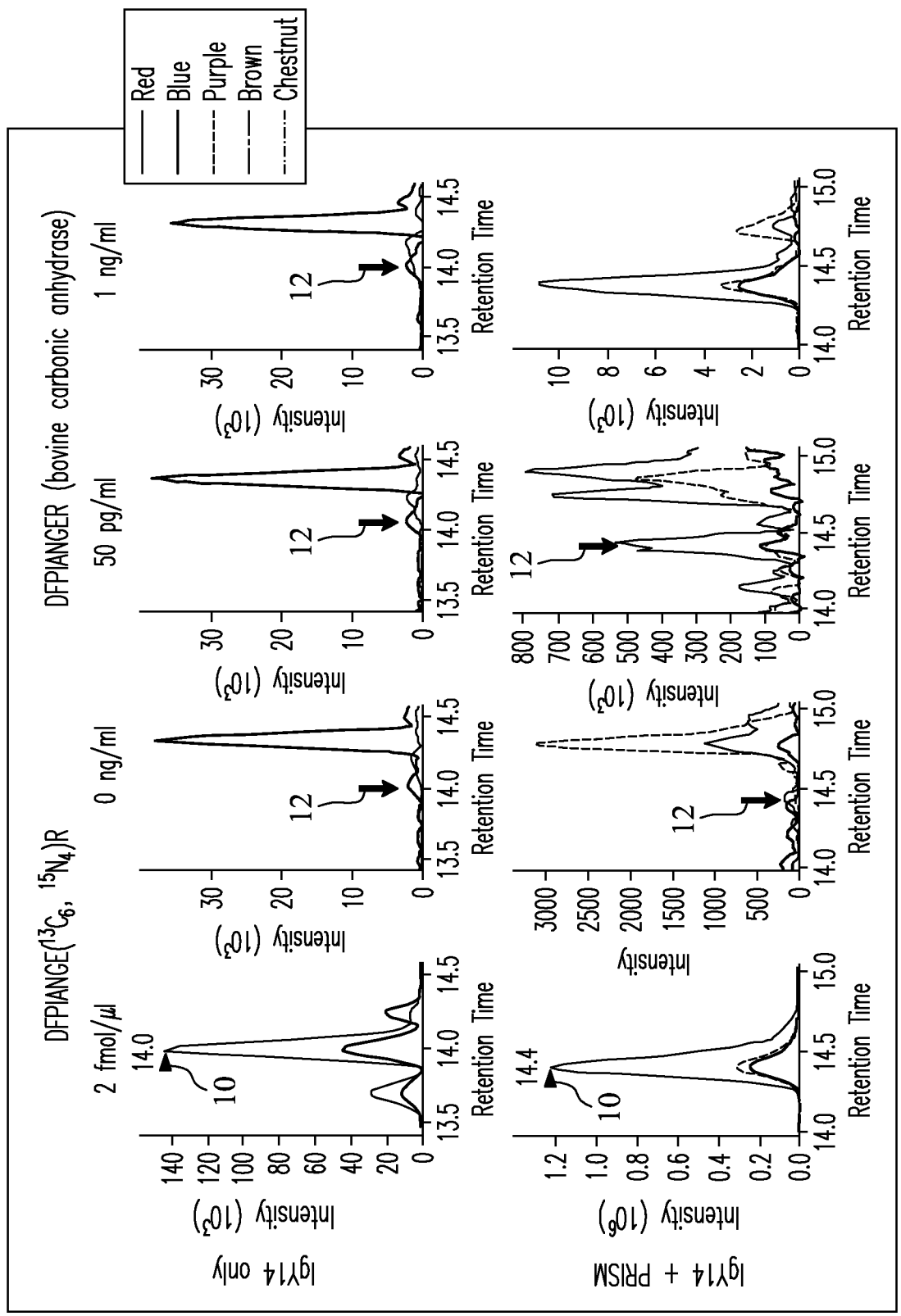
FIGS. 2a-2b show quantification results obtained for individual fractions and multiplexed fractions, respectively, derived from selected samples in accordance with the present invention.

Quantification of low-abundance target analytes has been demonstrated using peptide level calibration. FIG. 2a shows extracted ion chromatograms (XICs) of transitions monitored for the peptide DFPIANGER (SEQ. ID. NO. 1) derived from bovine carbonic anhydrase (BCA) at selected concentrations with and without application of PRISM: IgY14 only: 509.8/378.7 (red), 509.8/546.3 (blue); IgY14 plus PRISM: 509.8/378.7 (red), 509.8/756.5 (blue), 509.8/546.3 (purple). Black arrowheads 10 mark peak retention times of heavy internal standards. Arrows 12 indicate locations of SRM peaks for light (native) peptides based on the retention time of heavy internal standards.

TABLE 1 compares Limit of Detection (LOD) and Limit of Quantification (LOQ) values for four target proteins in plasma samples. Results obtained from IgY14 alone or from the combined IgY-PRISM approach in accordance with the present invention are presented.

Assays (ELISA). The present invention can also detect target analytes of interest including, but not limited to, e.g., selected protein biomarkers and signaling proteins (e.g., single-digit copies per cell) in cells or tissues, drugs, metabolites, and other low-abundance compounds in complex biological samples and systems including, e.g., blood plasma/serum samples. LOQ values obtained from the best transitions for each peptide from the four proteins demonstrate that PRISM improves SRM sensitivity by nearly 200-fold for six of the eight peptides. Two other peptides [DGPLTGTYR (SEQ. ID. NO. 2) and VDEDQPFPAVPK (SEQ. ID. NO. 5)] showed 20-fold and 5-fold LOQ improvements, respectively, attributed primarily to interference from co-eluting species.

Quantification with Protein Level Calibration

Estimation of Target Protein Concentrations

Quantification of low-abundance target analytes has been demonstrated with protein level calibration. Accurate absolute quantification of targets (e.g., proteins) can be obtained with SRM assays when calibrated against standards (e.g.,

TABLE 1

Summary of LOD and LOQ results for four target proteins in female plasma obtained with IgY14-PRISM compared to IgY14 only.

| Protein | Surrogate Peptide | Fractionation Strategy | LOD (ng/mL) | LOQ (ng/mL) |
|---|---|---|---|---|
| Bovine carbonic anhydrase | DFPIANGER (SEQ. ID. NO. 1) | IgY14 (only) | 5 | 10 |
| " | " | IgY14/PRISM | <0.05 | 0.05 |
| Bovine carbonic anhydrase | DGPLTGTTYR (SEQ. ID. NO. 2) | IgY14 (only) | 5 | 10 |
| " | " | IgY14/PRISM | 0.05 | 0.5 |
| Bovine β-lactoglobulin | VLVLDTDYKK (SEQ. ID. NO. 3) | IgY14 (only) | 0.5 | 5 |
| " | " | IgY14/PRISM | <0.05 | <0.05 |
| Bovine β-lactoglobulin | VYVEELKPTPEGDLEILLQK (SEQ. ID. NO. 4) | IgY14 (only) | 5 | 10 |
| " | " | IgY14/PRISM | <0.05 | <0.05 |
| E. coli β-galactosidase | VDEDQPFPAVPK (SEQ. ID. NO. 5) | IgY14 (only) | 10 | 25 |
| " | " | IgY14/PRISM | 0.5 | 5 |
| " | LWSAEIPNLYR (SEQ. ID. NO. 6) | IgY14 (only) | 10 | 100 |
| " | " | IgY14/PRISM | 0.05 | 0.1 |
| Protein-Specific Antigen (PSA) | IVGGWECEK* (SEQ. ID. NO. 7) | IgY14 (only) | 25 | 100 |
| " | " | IgY14/PRISM | 0.05 | 0.1 |
| " | LSEPAELTDAVK (SEQ. ID. NO. 8) | IgY14 (only) | 5 | 10 |
| " | " | IgY14/PRISM | <0.05 | <0.05 |

*Synthesized with carbamidomethyl cysteine.

Results show PRISM significantly reduces background interference levels and enhances signal-to-noise ratios (S/N) for analytes at these concentrations, i.e., 50 pg/mL and 1 ng/mL, providing highly sensitive SRM quantification of proteins. The approach can reliably quantify low-abundance proteins at sub-nanogram or low picogram per milliliter quantities in plasma/serum samples, including prostate-specific antigen (PSA) in clinical serum samples, and those that have a high correlation (i.e., >0.99) when compared with results obtained from Enzyme Linked Immunosorbent protein standards) to account for issues associated with digestion efficiency and sample losses. Light peptides derived from target proteins can be determined based on the peak area ratios of light (L) peptides (i.e., not labeled) to heavy (H) (i.e., labeled) peptides (L/H) when heavy synthetic peptides (internal standards) are spiked at known concentrations. These values can be used to estimate target protein concentrations to evaluate recovery and accuracy of PRISM-SRM assays. Target protein concentrations ($C_{pc}$) may be calculated in concert with Equation [1], as follows:

$$(C_{pc}) = \frac{[(L/H\{\text{area ratio}\}) \times (C_{is}\{\text{standard}\}) \times (\text{protein } MW) \times (\text{dilution factor})]}{[\text{protein recovery}]} \quad [1]$$

Here, (L/H) is the area ratio; ($C_{is}$) is the concentration of the internal standard (e.g., 2 pmol/mL); (protein MW) is the molecular weight of the protein; (dilution factor) is the dilution factor (e.g., 1.97 calculated as a ratio of the sample volumes [2.46 mL/1.25 mL]); and (protein recovery) is the protein recovery. To simplify calculations, complete digestion of target proteins may be presumed, which gives a 1:1 molar ratio between target peptides and respective target proteins. In exemplary tests, accuracy of the PRISM-SRM assay was tested by spiking tryptic digests of target proteins (containing peptide mixtures obtained from IgY14 flow-through) spiked with known levels of heavy peptide standards. Other data collected in concert with the present invention with their associated calculations are reported by Shi et al. in [Proceedings of the National Academy of Sciences of the United States of America (PNAS), Sep. 18, 2012, Vol. 109, No. 38, pgs. 15395-15400], which data are incorporated by reference in their entirety herein.

Figure 2B:
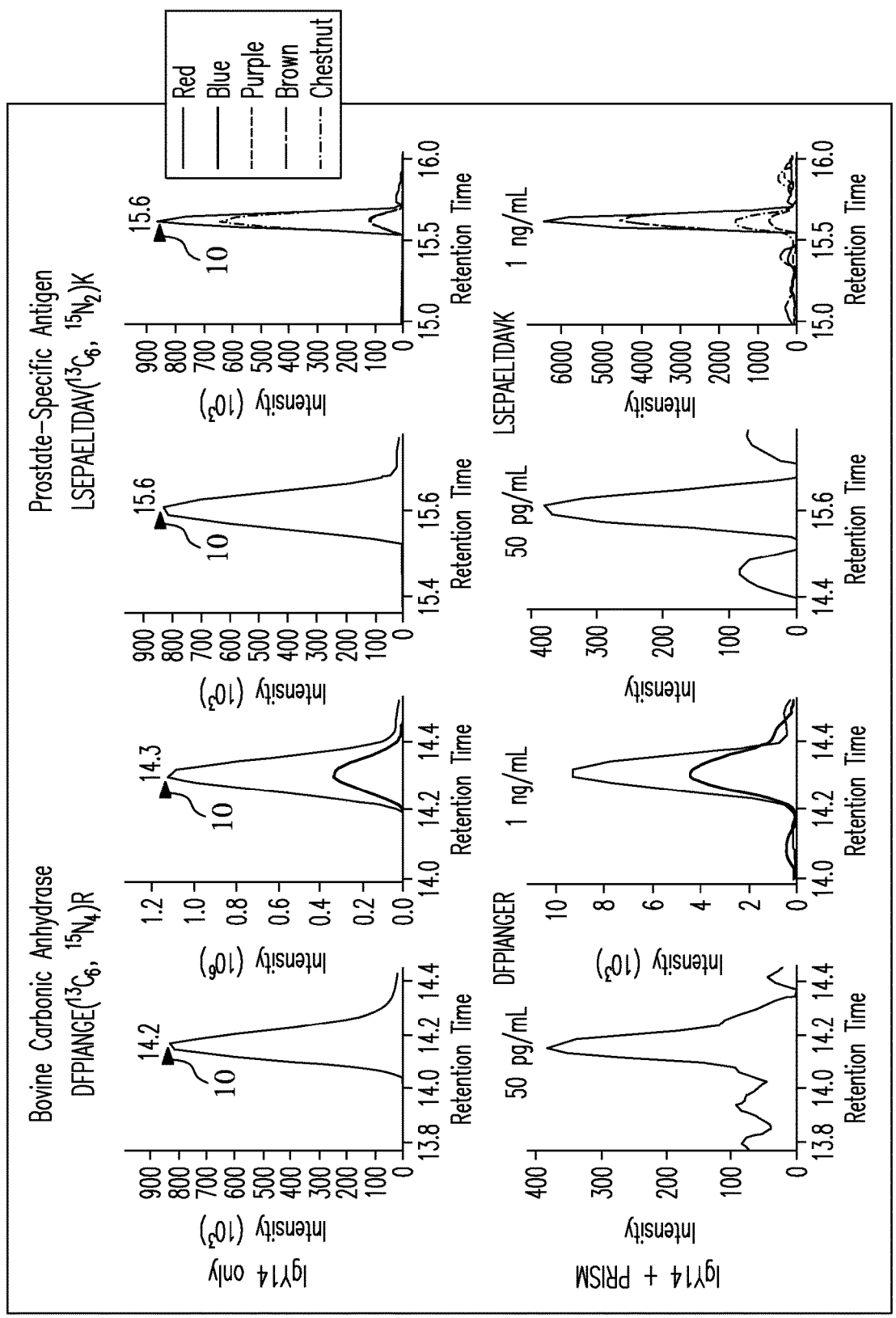

FIG. 2b shows XICs of transitions monitored for two peptides representing two target proteins (bovine carbonic anhydrase and PSA) at concentrations of 50 pg/mL and 1 ng/mL, respectively. In an exemplary test, a single LC-SRM analysis was performed containing eight target peptide fractions that were pooled (i.e., multiplexed) prior to the LC-SRM analysis. Internal standards were spiked at 2 fmol/pL. DFPIANGER (SEQ. ID. NO. 1): 509.8/378.7 (red), 509.8/546.3 (blue); LSEPAELTDAVK (SEQ. ID. NO. 8): 636.8/943.5 (red), 636.8/775.5 (brown), 636.8/846.5 (purple), 636.8/472.3 (chestnut). Black arrowheads 10 mark peak retention times of heavy internal standards.

Results show transitions monitored for the two peptides from the two target proteins (i.e., bovine carbonic anhydrase and PSA) at concentrations of 50 pg/mL and 1 ng/mL, respectively. SRM signals for the analyses are similar to those obtained from individual peptide fractions, as reflected by the signals of both light and heavy peptides at two representative concentrations (e.g., 50 pg/mL and 1 ng/mL). Noted exceptions were the two most hydrophobic peptides, VYVEELKPTPEGDLEILLQK (SEQ. ID. NO. 4) from Bovine β-lactoglobulin and LWSAEIPNLYR (SEQ. ID. NO. 6) from E. coli β-galactosidase, where SRM signals dropped ~3- and ~100-fold, respectively, for the pooled samples. Results are attributed to loss of hydrophobic peptides stemming from pooling and sample lyophilization. Loss of hydrophobic peptides can be minimized by substituting an isopropanol water mixture for water solvent during collection into the 96-well plate. Results show that four to eight fractions having different elution times may be multiplexed without affecting second-dimension separation significantly due to the partial orthogonality that exists between first-dimension high-pH, and the second-dimension low-pH, reversed-phase LC fractions.

Figure 2C:
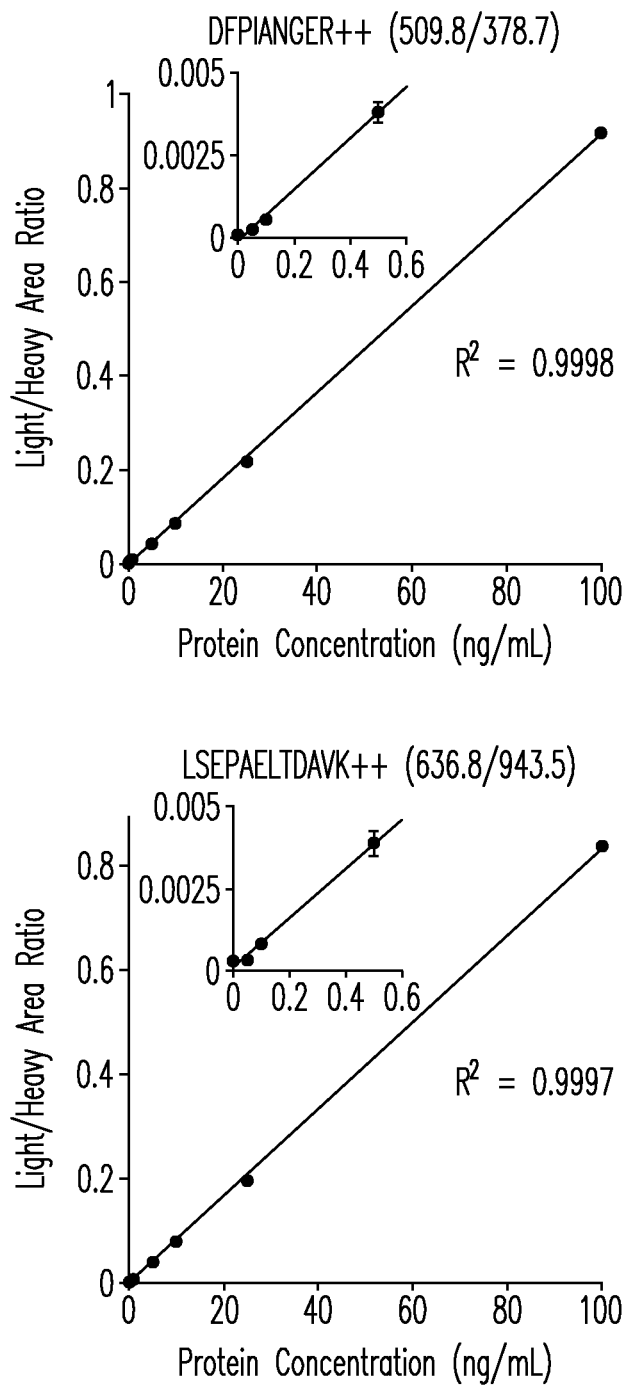
FIG. 2c shows a typical calibration curve for quantifying low-abundance target analytes in accordance with the present invention.

PRISM-SRM protein concentrations were also calculated for four target proteins based on the L/H area ratio of the best transition. FIG. 2c shows a typical calibration curve for quantifying low-abundance target analytes in accordance with the present invention. In the figure, two representative transitions are shown for the peptides DFPIANGER (SEQ. ID. NO. 1) and LSEPAELTDAVK (SEQ. ID. NO. 8), which are peptides derived from bovine carbonic anhydrase and PSA, respectively. All four target proteins displayed a good correlation between calculated and expected protein concentrations except E. coli β-galactosidase, with an approximate 1:1 molar ratio. These results show that high accuracy can be achieved with PRISM-SRM assays. Calculated concentrations for E. coli β-galactosidase deviated significantly from expected concentrations below 1 ng/mL, which was attributed to substantial background interferences.

Multiplexing Fractions for Throughput

Potential for higher throughput analysis was tested. Following i-Selection, six fractions including eight target peptides were pooled and concentrated to a final volume of ~20 μL (i.e., the same volume as the original single fraction). All target peptides were spiked with internal standards at a concentration of 2 fmol per μL. Fraction multiplexing was further assessed by spiking 42 non-human target peptides (21 light and 21 heavy peptides) spiked into a non-depleted human serum sample. All target peptides were spiked at a 5 attomol/μL level (~ng/mL level of target proteins). Two levels of fraction multiplexing were assessed, with all 96 fractions being concatenated into 12 or 6 final fractions regardless of whether the fraction contained target peptides. TABLE 2 present results.

TABLE 2 compares S/N and L/H for multiplexed (or post-concatenated) fractions, and individual fractions, respectively.

| Peptide | Multiplexed Fraction | | Individual Fraction | | Relative Error |
|---|---|---|---|---|---|
| | S/N | L/H | S/N | L/H | (%) [b] |
| DFPIANGER (SEQ. ID. NO. 1) | 10.0 | 0.001481 | 3.3 | 0.001517 | 2.4 |
| DGPLTGTYR (SEQ. ID. NO. 2) | 24.2 | 0.000467 | 10.2 | 0.0004476 | 4.3 |
| IVGGWECEK (SEQ. ID. NO. 7) | 18.2 | 0.000595 | 16.7 | 0.0006255 | 4.9 |
| LSEPAELTDAVK (SEQ. ID. NO. 8) | 11.3 | 0.0005023 | 19.8 | 0.0006936 | 27.6 |

TABLE 2-continued compares S/N and L/H for multiplexed (or post-concatenated) fractions, and individual fractions, respectively.

| Peptide | Multiplexed Fraction | | Individual Fraction | | Relative Error |
|---|---|---|---|---|---|
| | S/N | L/H | S/N | L/H | (%) [b] |
| AGTFVAAR (SEQ. ID. NO. 9) | 7.1 | 0.001551 | 40.0 | 0.00144 | 7.7 |
| SDVGALLK (SEQ. ID. NO. 10) | 50.0 | 0.003813 | 58.8 | 0.004248 | 10.2 |
| ELGPSPIK (SEQ. ID. NO. 11) | 3.6 | 0.002191 | 9.8 | 0.002085 | 5.1 |
| VSSIIEPR (SEQ. ID. NO. 12) | 105.9 | 0.00112 | 16.7 | 0.00158 | 29.1 |
| IVADEMVK (SEQ. ID. NO. 13) | 45.5 | 0.002103 | 8.3 | 0.00134 | 56.9 |
| ALEAVEAAR (SEQ. ID. NO. 14) | 1.3 | 0.001766 | 3.1 | 0.00171 | 3.3 |
| VNDAGIIER (SEQ. ID. NO. 15) | 7.7 | 0.002197 | 14.3 | 0.0019 | 15.6 |
| WEVSPTTR (SEQ. ID. NO. 16) | 15.4 | 0.001111 | 28.6 | 0.000939 | 19.1 |
| DLEVISSQR (SEQ. ID. NO. 17) | 45.5 | 0.003393 | 14.3 | 0.003026 | 12.1 |
| MVGTNPDTVK (SEQ. ID. NO. 18) | 55.6 | 0.001125 | 16.7 | 0.00161 | 30.1 |
| DNDNPFELVR (SEQ. ID. NO. 19) | 10.9 | 0.001487 | 529.2 | 0.00147 | 1.2 |
| NSFPGDEIPIVR (SEQ. ID. NO. 20) | 10.1 | 0.000841 | 13.1 | 0.000685 | 22.8 |
| YQGTPEDNLR (SEQ. ID. NO. 21) | 50.0 | 0.002446 | 50.0 | 0.002136 | 11.3 |
| FEGAATETSYER (SEQ. ID. NO. 22) | 20.1 | 0.002446 | 11.1 | 0.002536 | 3.5 |
| AQIEETESAFDR (SEQ. ID. NO. 23) | 1.2 | 0.002275 | 6.7 | 0.002504 | 9.2 |
| GAAPASAAAAEEAPAEDK (SEQ. ID. NO. 24) | 45.5 | 0.0009235 | 100.2 | 0.0006205 | 48.8 |
| LYTLTPEYGAPGR [a](SEQ. ID. NO. 25) | 50.0 | 0.001515 | 20.1 | 0.001275 | 18.7 |

[a] Cysteine was synthesized as carbamidomethyl cysteine.
[b] Each light and heavy peptide has a concentration of 5 atmol/μL and 5 fmol/μL, respectively.

Multiplexing of 96 fractions into 12 fractions still provides similar PRISM-SRM sensitivity for detecting target proteins at levels close to the LOQ compared with the SRM measurements of each individual peptide fraction. However, sensitivity was significantly reduced when fractions were multiplexed into a total of six final fractions due to increased sample complexity and background interference levels.

Overall results demonstrated the utility of i-Selection and multiplexing steps to enhance overall PRISM-SRM throughput, which is comparable to, and can be even better than conventional LC-SRM performed with limited SCX fractionation (e.g., 8 to 12 fractions). For example, even with limited fraction multiplexing (concatenation), moderate throughput (e.g., defined by a quantity of up to ~50 sample analyses per week depending upon experimental details) can be achieved in concert with the present invention. For example, when quantifying a relatively large number of proteins (i.e., 100), all 96 selected fractions may contain target peptides. However, in some applications, fractions can be carefully combined, e.g., into 12 multiplexed fractions based on peptide elution times to achieve moderate throughput. Calibration curves for PRISM-SRM assays for the four target proteins demonstrated excellent linearity over a concentration range from about 50 pg/mL to about 100 ng/mL.

Reproducibility of PRISM-SRM (in terms of coefficient of variation (CV) values from triplicate measurements) is comparable to or better than conventional SRM, where a CV of 10% can be typically achieved. The improved reproducibility is attributed to an improved S/N.

PRISM-SRM reproducibility was evaluated by analyzing three processing replicates (1 ng/mL for each target protein in IgY14-depleted plasma). Average CV across all of the processing replicates was 5.5%, which exemplifies the high precision capability of the invention for quantifying low-abundance proteins in human plasma. Reliable quantification, sensitivity, and reproducibility of target proteins is demonstrated even at concentrations between about 50 pg/mL and about 100 pg/mL in plasma/serum samples.

Quantification of PSA in Clinical Serum Samples

The PRISM-SRM assay without IgY14 depletion can be used to quantify PSA, e.g., in serum samples collected, e.g., from prostate cancer patients. Clinical serum samples from patients undergoing PSA testing for prostate cancer were provided by Johns Hopkins Medical Institutions. In exemplary tests, approximately 2 µL of serum (~100 µg) from each of eight patients was directly subjected to trypsin digestion followed by PRISM-SRM. XICs (not presented) showed that PRISM-SRM assays without depletion enable quantification of PSA in clinical serum samples down to sub-nanogram per milliliter levels.

Figure 3:
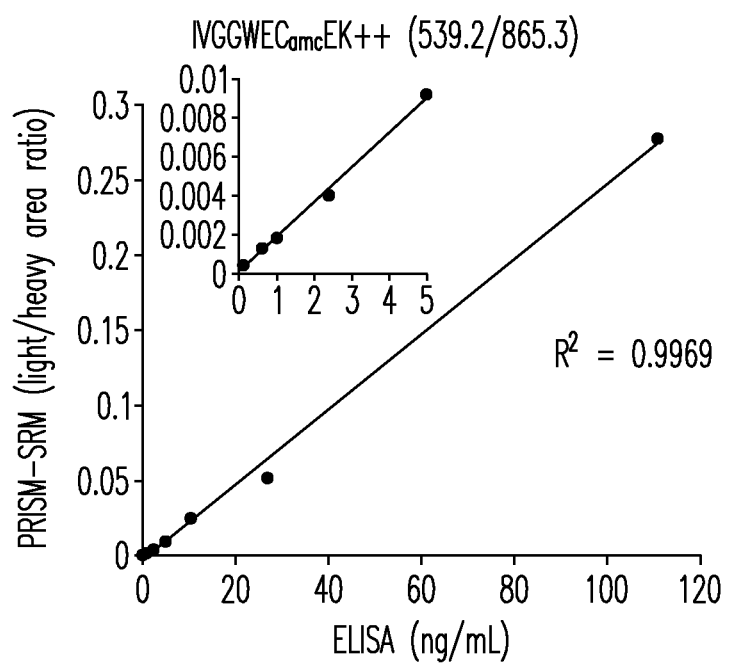
FIG. 3 compares results for prostate-specific antigen (PSA) obtained in accordance with the present invention against those obtained from a conventional immunoassay.

FIG. 3 compares quantification results for PRISM-SRM compared against ELISA measurements for PSA in patient serum samples. Excellent correlation is observed between the PRISM-SRM assay and ELISA results. PRISM-SRM assay results are attributed to a high reproducibility and peptide recovery obtained using the high-pH reversed-phase cLC in the PRISM workflow as opposed to use of a SISCAPA assay or SCX fractionation strategy. Slope of the correlation curve is ~3.55, which indicates that the PRISM-based assay quantifies ~3 times more PSA than does ELISA. Results may be attributed to differences in recognition of differential epitope of various PSA forms. ELISA depends on antibody affinity for each PSA form; PSA in blood sera can remain free and also can form complexes with other proteins (e.g., PSA-ACT, PSA-α2M). An antibody may not be able to recognize all forms of PSA. In contrast, PRISM-SRM measures total PSA concentration in the serum sample.

Accuracy of the PRISM-SRM approach has also been demonstrated for quantifying PSA in female plasma at the peptide level, which showed a nearly 1:1 correlation between calculated and expected PSA concentrations).

PSA recovery during sample processing can also be estimated at the protein level. Protein-level PSA recovery following IgY14 depletion, trypsin digestion, and sample cleanup (~13%), e.g., may be determined by dividing the L/H area ratio at the protein level by that at the peptide level, e.g., at a PSA concentration of 10 ng/mL. Recovery is consistent with measured recovery values for PSA protein in human plasma after flowing through an IgY12-depletion column. Using PSA protein recovery during sample processing and the L/H ratio from the PRISM-SRM measurement, PSA concentrations at the protein level can be calculated.

Results demonstrate that PSA peptide LSEPAELTDAVK (SEQ. ID. NO. 8) may be readily detected in all female serum samples spiked with PSA at 50 pg/mL or higher concentrations. Findings illustrate the robustness of the PRISM-SRM assay both in terms of accuracy and precision for quantifying PSA concentrations in serum samples up to 50 pg/mL or 100 pg/mL. Results further demonstrate the high sensitivity of the PRISM-SRM assay.

Quantification of Protein Isoforms in a Prostate Cancer Cell Line

LC-SRM can detect and quantify levels of protein isoforms or mutant proteins in cells, tissues, and biofluids. An LC-SRM assay was used to measure endogenous levels of two protein isoforms from a vertebral cancer cell line (VCaP) derived from a patient with hormone-refractory metastatic prostate cancer obtained from the American Type Culture Collection (Manassas, Va., USA). Two protein isoforms taken from a VCaP cell line were obtained commercially. The protein isoforms were derived from a TMPRSS2-ERG fusion of: 1) a full-length prototypical ETS-Related Gene (ERG) protein and 2) an artificially constructed Degenerated E-26 Transformation Specific (i.e., dETS) protein. The latter protein lacks the ETS domain, a portion of the protein sequence that can exist and function independently of the rest of the protein chain. While the LC-SRM assay did not provide sufficient sensitivity to confidently detect and quantify either protein isoform, both a commonly shared peptide NTGGAAFIFPNTSVYPEATQR (SEQ. ID. NO. 26) and an ERG-specific peptide (or erythroblastosis virus E-26 oncogene-specific peptide) FDFH-GIAQALQPHPPESSLYK (SEQ. ID. NO. 27) were readily detected and quantified by the PRISM-SRM assays. However, the SRM signal from a dETS-specific peptide LANPGSGQFHGIAQALQPHPPESSLYK (SEQ. ID. NO. 28) was not observed, which confirmed that the dETS protein variant was not expressed in the VCaP prostate cancer cell line (a negative control). The L/H area ratio of the SRM signal from the commonly shared peptide was 0.425, which is much higher than the signal for the ERG-specific peptide (0.113), suggesting that other TMPRSS2-ERG fusion variants may be expressed in the VCaP cancer cell line.

PRISM-SRM represents a major technological advancement, e.g., for quantification of trace levels (e.g., pg/mL) of a wide range of target analytes in complex biological systems (such as blood plasma) without need of specific antibodies for enrichment. For example, the method can effectively enrich target peptides in preparation for, e.g., LC-SRM analyses. PRISM-SRM combined with LC-SRM also represents an important advance in detecting very-low-abundance proteins in biofluids and cells without the need for specific affinity reagents. For example, the antibody-free approach and high-sensitivity features of PRISM-SRM are particularly useful for quantification of low-abundance proteins in biofluids, cells, or tissues in biomarker pre-verification and systems-biology studies. Furthermore, PRISM-SRM is relatively simple to implement, requiring only commercially available reagents and instruments. Ability to detect subtle changes in protein abundances and modifications in clinical specimens by targeting specific protein pathways may be useful for gaining insights into disease biology and developing drug or therapeutic targets. Results presented herein demonstrate reliable quantification of target proteins for concentrations between about 50 pg/mL to 100 pg/mL in plasma/serum samples.

The following examples provide a further understanding of various aspects of the present invention in its larger aspects.

EXAMPLE 1

Blood Plasma and Serum Depletion

Fourteen high abundance plasma proteins (albumin; IgG; α1-antitrypsin; IgA; IgM; transferrin; haptoglobin; α1-acid glycoprotein; α2-macroglobulin; apolipoprotein A-I; apolipoprotein A-II; fibrinogen; complement C3; and apolipoprotein B) that constitute ~95% of the total protein mass of human plasma were depleted from plasma and serum samples using a Seppro® IgY-14 LC10 immunoaffinity column (Sigma-Aldrich, St. Louis, Mo., USA) on an Agilent 1100 series HPLC system (Agilent, Palo Alto, Calif., USA). For each depletion experiment, ~125 µL plasma/serum was diluted 10-fold and injected onto the IgY14 column. Following the IgY14 separations, the flow-through fraction was concentrated using Amicon® Ultra-15 (5 kDa nominal molecular weight limit, Millipore, Billerica, Md., USA). Protein concentrations were determined by BCA protein assay (Pierce, Rockford, Ill.).

EXAMPLE 2

Protein Digestion and Spike-In Experiments

Protein samples from plasma/serum and cancer cells were digested with the same protocol. For the plasma spike-in experiments at the peptide level, IgY14 flow-through proteins from 10 injections were pooled, denatured, and then reduced using 8 M urea and 10 mM dithiothreitol (DTT) in 50 mM $NH_4HCO_3$ buffer (pH 8.0) for 1 h at 37° C. Samples were then alkylated using 40 mM iodoacetamide for 1 h at room temperature. The resulting protein mixture was diluted 6-fold with 50 mM $NH_4HCO_3$, after which sequencing grade modified porcine trypsin (Promega, Madison, Wis.) was added at a trypsin:protein ratio of 1:50 (w/w), and the sample digested at 37° C. for 3 hrs. The protein digest was subsequently cleaned up using an SPE_C-18 column (Supelco, Bellefonte, Pa.). The final peptide samples were stored at −80° C. until further usage. Proteins from plasma/serum and cancer cells samples were digested with the same protocol. Stocks of 1 µg/µL of each of the four digested target proteins were spiked into the IgY14 flow-through peptide mixture to provide final concentrations of 0, 0.05, 0.1, 0.5, 1, 5, 10, 25, and 100 ng/mL for each protein. A concentration of 2 fmol/µL of each heavy peptide standard was also added to each sample. For protein-level spike-in experiments, PSA was spiked into the female serum samples to reach final concentrations of 0, 0.05, 0.1, 0.3, 1, 2.5, 5, and 10 ng/mL before the IgY14 depletion. Each female serum sample was subjected to triplicated IgY14 depletion, starting with 125 µL original serum for each replicate. IgY14 flow-through for each sample was digested and concentrated as described above. All peptide sample stocks at different spike-in levels were individually diluted to 0.5 µg/µL and then heavy synthetic peptide standards were added to a final concentration of 2 fmol/µL.

EXAMPLE 3

SRM Assay Configuration

SRM assays were configured based on experimental tandem MS/MS data for peptide mixtures from four target proteins: 1) bovine carbonic anhydrase, 2) bovine β-lactoglobulin, 3) *E. coli*β-galactosidase, and 4) human prostate-specific antigen (PSA) (Sigma-Aldrich, St. Louis, Mo., USA). MS/MS spectra were used to select transitions by choosing the eight most intense y-type ions for each peptide of precursor charge state +2 or +3. For each target protein, two unique peptides were selected that had the best ionization and most intense fragmentation patterns when transmitted to the mass spectrometer. Precursor-to-fragment ion transitions (TABLE 1) were tested by SRM measurements on a TSQ Quantum Ultra triple quadrupole mass spectrometer (Thermo Fisher Scientific, Inc., Waltham, Md., USA). Optimization of collision energy (CE) was performed by direct infusion of a 500 nM digested solution of each target protein dissolved in 0.1% formic acid in water at an infusion rate of 300 nL/min. Four best transitions for each target peptide were selected for further analysis and the two most intense transitions were used for quantifying target proteins and evaluating reproducibility of PRISM-SRM assays (TABLE 1).

EXAMPLE 4

High-pH Reversed-Phase cLC Fractionation

The tryptic digest of the IgY14 flow-through fraction spiked with internal standard (IS) heavy peptides was separated by high resolution reversed-phase capillary LC (cLC) systems (200 µm i.d.×50 cm length) using high pH mobile phases. ~20 µg of a plasma digest spiked with internal standard (IS) heavy peptides containing peptide mixtures was injected and loaded onto the cLC column and separated by a high-resolution, reversed-phase capillary LC (i.e., cLC) system using high-pH mobile phases in a nanoacquity UPLC® system (Waters Corp., Milford, Md., USA) equipped with an autosampler (FIG. 1a). Capillary columns, 200 µm i.d.×50 cm long, were packed with 3 µm Jupiter C18 bonded particles (Phenomenex, Torrence, Calif., USA). Separations were performed at a flow rate of 3.3 µL/min on binary pump systems, using 10 mM ammonium formate (pH 10) as mobile phase A, and 10 mM ammonium formate in 90% acetonitrile (pH 10) as mobile phase B. 45 µL of peptide mixtures (0.5 µg/µL) were typically loaded onto the column and separated using a binary gradient of 5-15% B in 15 min, 15-25% B in 25 min, 25-45% B in 25 min, and 45-90% B in 38 min.

Following the LC separations, eluent from the capillary cLC column was split into two flowing streams (split ratio: 1:10) via a Tee union. A small eluent fraction (~9%) from the cLC column was introduced to a triple quadrupole mass spectrometer (e.g., TSQ Quantum Ultra, Thermo Fisher Scientific Inc., Waltham, Md., USA) at a flow rate of 300 nL/min for on-line SRM monitoring of heavy IS-marked peptides. The TSQ Quantum Ultra for SRM monitoring was operated with ion spray voltages of 2400±100 V, a capillary offset voltage of 35 V, a skimmer offset voltage of −5 V, and a capillary inlet temperature of 220° C. Tube lens voltages were obtained from automatic tuning and calibration without further optimization. Q1 and Q3 stages were set at unit resolution of 0.7 FWHM. Q2 gas pressure was 1.5 mTorr. Scan width of 0.002 m/z and a dwell time of 25 ms were used. A large eluent fraction (~91%) from the cLC column was automatically transferred using the Triversa NanoMate® system (Advion BioSciences, Ithaca, N.Y., USA) and collected at a rate of one minute per fraction into a 96-well plate at a flow rate of 3 µL/min over the course of the LC separation run (e.g., 120 min). Prior to peptide fraction collection, 17 µL of water was added to each well in the plate to avoid peptide loss and also to dilute the peptide fraction (nearly 1:7 dilution) for direct LC-SRM analysis. Specific target peptide fractions were selected based on the elution times of IS peptides being monitored by on-line SRM.

EXAMPLE 5

Intelligent Selection and Fraction Multiplexing

With on-line SRM monitoring of heavy isotope labeled synthetic internal standards during the first dimensional high pH reversed phase separation, the accurate elution profiles of the specific internal standards was generated, allowing precise determination of the locations of target peptide fractions in the 96-well plate and enabling the selection of target peptide containing fractions (termed i-Selection) for downstream LC/SRM analyses. A target peptide may be spread across multiple LC fractions, and only the most abundance target peptide fraction was selected for subsequent quantification. To improve the overall sample throughput, a limited number of target fractions eluted at different times during the first dimension separation can be multiplexed prior to nanoLC-SRM. Fractions containing target peptides were selected having the same elution times as those of the internal standard (i.e., isotope-labeled surrogates). Fractions (individual or multiplexed) were monitored and selected via i-Selection in concert with on-line SRM. For example, light (unlabeled) peptides (L) from target proteins may have the same chemical properties, (e.g., elution time, transition ratio, and like properties) as those containing heavy internal standards. Here, the heavy (isotope-labeled) internal standard has a slightly greater molecular weight, but an identical elution profile.

Fractions that elute at early, middle, and late retention times with little overlap in their elution profiles during the second dimension LC separation can be combined for efficient use of second dimensional separation space. For example, in the exemplary process, 96 fractions collected in the first-dimension LC separation can be multiplexed into 12 fractions by combining 8 fractions from the first-dimension LC separation into 1 fraction for downstream LC-SRM analyses. For example, multiplexed fraction 2 may include fractions 2, 14, 26, 38, 50, 62, 74, and 86 (bolded in the figure) into one sample from the first dimensional LC separation for second-dimension LC-SRM analysis (described in reference to FIG. 1b hereinabove). However, number of fractions is not intended to be limited. In addition, with the elution profiles of target peptides from the on-line SRM monitoring, it is feasible to generate a relatively small number of multiplexed fractions for subsequent LC-SRM analyses by combining only the most informative target peptide fractions without including all peptide fractions.

EXAMPLE 6

LC-SRM Analysis

Following i-Selection, a target peptide fraction was either directly subjected to LC-SRM measurement or multiplexed with other target fractions prior to LC-SRM analysis, as detailed hereafter. Following i-Selection and multiplexing of target peptide fractions, the peptide fraction of interest was subjected to LC-SRM analysis. Pooled peptide fractions were dried to approximately the same volume (~20 µL) as the individual peptide fractions. All peptide fractions were analyzed using a nanoacquity UPLC system coupled on-line to a triple quadrupole (e.g., TSQ Vantage) mass spectrometer (Thermo Fisher Scientific, Inc., Waltham, Md., USA). Solvents consisted of 0.1% formic acid in water (mobile phase A) and 0.1% formic acid in 90% acetonitrile (vol/vol, mobile phase B). Peptide fractions were loaded at 10 uL/min with 3% mobile phase B onto a C18 trap column (180 um i.d.×20 mm) for 5 minutes. Peptide separations were performed at a flow rate of 400 nL/min, using an ACQUITY UPLC BEH 1.7 µm C18 column [75 µm i.d.×25 cm] (Waters Corp., Milford, Md., USA), which was connected to a chemically etched 20 um i.d. fused silica emitter via a Valco stainless steel union. 4 µL sample was injected for LC-SRM using a binary gradient of 10-20% B in 7 min, 20-25% B in 17 min, 25-40% B in 1.5 min, 40-95% B in 2.5 min, and 95% B for 6 min. The TSQ Vantage was operated in the same manner as the TSQ Quantum Ultra with a scan width of 0.002 m/z and dwell time of 40 ms for all SRM transitions.

EXAMPLE 7

Data Analysis

SRM data acquired on the TSQ Vantage were analyzed using Xcalibur 2.0.7 (ThermoFisher Scientific, Waltham, Mass., USA). Two most abundant transitions for each peptide were used for quantification (TABLE 1). Peak detection and integration were based on two criteria: 1) the same retention time and 2) approximately the same relative SRM peak intensity ratios across multiple transitions between light peptide and heavy peptide standards. All data were manually inspected to ensure correct peak detection and accurate integration. Signal to noise ratio (S/N) was calculated by the peak apex intensity over the highest background noise in a retention time region of ±15 seconds for target peptides. Background noise levels were estimated by visually inspecting chromatographic peak regions. LOD and LOQ values were defined as the lowest concentration point of target proteins at which the signal-to-noise (S/N) ratio of surrogate peptides was at least 3 and 10, respectively. The SRM peak area ratio (L/H) of light (L) to heavy peptides (H) was used to generate calibration curves and to evaluate reproducibility. All calibration and correlation curves were plotted using Microsoft Excel® 2007. Raw data obtained from the TSQ Vantage (without further processing) were loaded into Skyline software (MacCoss Laboratory, University of Washington, Seattle, Wash., USA) to create high-resolution figures of extract ion chromatograms (XICs) of multiple transitions monitored for target proteins.

While preferred embodiments of the present invention have been shown and described, it will be apparent to those of ordinary skill in the art that many changes and modifications may be made without departing from the invention in its true scope and broader aspects. The appended claims are therefore intended to cover all such changes and modifications as fall within the scope of the invention.

What is claimed is:

1. A two-dimensional process for quantifying low-abundance target analytes in an entire complex sample, comprising the steps of:
   partitioning the complex sample into a HAP sample fraction and an LAP sample fraction;
   spiking the LAP sample fraction with a known quantity of at least one isotope-labeled target analyte having a pre-identified signal peak characteristic to form a spiked sample;
   performing a first dimension fractionation and selection on the spiked sample, the first dimension fractionation and selection comprising:
      fractionating the spiked sample to produce a plurality of first individual fractions;
      identifying one or more first individual fractions having the pre-identified signal peak characteristic and selecting the identified one or more of the first identified individual fractions, wherein at least two or more of the identified and selected fractions have different elution times;
      collecting the identified one or more first individual fractions in one or more wells of a first collection plate, the collection plate comprising a first set of columns and rows of wells, the first set of columns and rows defining a dimensional array wherein the number of wells can range between 96 and 400;
   performing a second dimension fractionation and selection on the identified one or more first identified fractions from within the one or more wells of the first collection plate, the second dimension fractionation and selection comprising:
      fractionating the identified one or more first identified fractions to produce a plurality of second individual fractions using a high-resolution chromatography device;
      identifying one or more of the plurality of second individual fractions having the pre-identified signal peak characteristic and selecting the identified plurality of second individual fractions;
      determining individual first detected peak areas for each pre-identified signal peak of each of the identified one or more of the plurality of second individual fractions;
      determining individual second detected peak areas for each low-abundance target analyte signal peak of the identified one or more of the plurality of second individual fractions; and
   quantifying the low-abundance target analytes in the sample from the ratio of the individual first detected peak area and the individual second detected peak area.

2. The process of claim 1 wherein the first dimension fractionation and selection further includes combining one or more of the identified one or more individual fractions into one or more wells of a second collection plate, wherein the second collection plate is the dimensional array of the first collection plate.

3. The process of claim 2 wherein the combining is performed with an N-well plate or a multi-dimensional array.

4. The process of claim 2 wherein the combining includes sorting the identified one or more individual fractions containing the low-abundance target analytes of a similar mass into one or more wells as the one or more individual fractions elute from the high-resolution chromatography device.

5. The process of claim 1 wherein the identifying the one or more first or second individual fractions includes detecting an SRM signal of the isotope-labeled target analyte in the one or more first or second individual fractions in real time prior to selecting the individual fractions.

6. The process of claim 1 wherein the identifying the one or more of the first or second individual fractions includes separating the selected individual fractions from the high-resolution chromatography device with a high-resolution separation process selected from the group consisting of: reversed-phase liquid chromatography, hydrophilic interaction chromatography, electrostatic repulsion hydrophilic interaction chromatography, capillary electrophoresis, or other chromatography separations, and combinations thereof.

7. The process of claim 1 wherein quantifying the low-abundance target analytes in the sample includes quantifying at a limit of detection, measured in blood plasma or serum, of at least about 100 pg/mL or better.

8. The process of claim 1 wherein the identifying the one or more of the first or second individual fractions includes monitoring the identifying the one or more of the first or second individual fractions released from the high-resolution chromatography device with a process selected from: on-line SRM monitoring, on-line UV detection monitoring, off-line screening, or combinations thereof.

9. The process of claim 1 wherein the identifying individual fractions includes monitoring the identifying the one or more of the first or second individual fractions released from the high-resolution chromatography device with a mass-selective instrument or a UV detection device.

10. The process of claim 1 wherein the identifying the one or more of the first or second individual fractions includes discarding individual fractions released from the high-resolution chromatography device that do not include the isotope-labeled target analyte.

\* \* \* \* \*